(12) United States Patent
Goldman et al.

(10) Patent No.: US 11,698,370 B2
(45) Date of Patent: Jul. 11, 2023

(54) HOME TOILET SYSTEM FOR MONITORING URINE COMPONENTS IN REAL TIME WHILE URINATION

(71) Applicant: OLIVE DIAGNOSTICS LTD., Jerusalem (IL)

(72) Inventors: Guy Goldman, Jerusalem (IL); Yaniv Oiknine, Ness-Ziona (IL); Ofer Melamed, Rehovot (IL)

(73) Assignee: OLIVE DIAGNOSTICS LTD, Jerusalem (IL)

( * ) Notice: Subject to any disclaimer, the term of this patent is extended or adjusted under 35 U.S.C. 154(b) by 0 days.

(21) Appl. No.: 17/449,411

(22) Filed: Sep. 29, 2021

(65) Prior Publication Data

US 2022/0244238 A1 Aug. 4, 2022

Related U.S. Application Data

(60) Provisional application No. 63/198,115, filed on Sep. 29, 2020, provisional application No. 63/198,114, filed on Sep. 29, 2020.

(51) Int. Cl.
*G01N 33/52* (2006.01)
*G01N 21/25* (2006.01)
(Continued)

(52) U.S. Cl.
CPC .............. *G01N 33/52* (2013.01); *E03D 9/00* (2013.01); *G01N 21/255* (2013.01); *G01N 21/31* (2013.01);
(Continued)

(58) Field of Classification Search
CPC .. G01N 33/493; G01N 33/52; G01N 33/4833; G01N 21/31; G01N 21/25; E03D 9/00; E03D 11/13; A61B 10/0038
See application file for complete search history.

(56) References Cited

U.S. PATENT DOCUMENTS 5,730,149 A 3/1998 Nakayama et al.
6,028,520 A 2/2000 Maehre
(Continued)

FOREIGN PATENT DOCUMENTS

JP 2019024933 A * 2/2019
KR 20100007389 A * 7/2008 ........... A47K 13/305
(Continued)

OTHER PUBLICATIONS

Xiaofeng Zhang, "Time-Resolved Synchronous Fluorescence for Biomedical Diagnosis", 2015 (Year: 2015).*

*Primary Examiner* — Maurice C Smith
(74) *Attorney, Agent, or Firm* — Reches Patents

(57) ABSTRACT

A system for urine sample analysis, the system may include one or more transmitters for transmitting radiation; one or more sensors that are configured to receive received radiation that passed through the urine sample and to generate detection signals indicative of an intensity of the received radiation at multiple frequencies; detaching elements that are configured to detach the one or more transmitters and the one or more sensors to a toilet bowl; and a processor that is configured to participate in the urine sample analysis for determining a content of the urine sample based on the detection signals.

23 Claims, 17 Drawing Sheets

(51) Int. Cl.
    *G01N 21/64*     (2006.01)
    *G01N 21/31*     (2006.01)
    *E03D 9/00*     (2006.01)
    *G01N 21/59*     (2006.01)
    *G01N 33/493*     (2006.01)

(52) U.S. Cl.
    CPC ......... *G01N 21/59* (2013.01); *G01N 21/6486* (2013.01); *G01N 33/493* (2013.01); *G01N 2021/3137* (2013.01)

(56) References Cited

U.S. PATENT DOCUMENTS

| | | | |
|---|---|---|---|
| 6,178,569 | B1 | 1/2001 | Quintana |
| 8,802,442 | B2 * | 8/2014 | Wheeldon .............. G01N 21/75 436/66 |
| 10,376,246 | B2 * | 8/2019 | Kashyap ................ G01N 21/31 |
| 2003/0029915 | A1 | 2/2003 | Barkan et al. |
| 2005/0036147 | A1 | 2/2005 | Sterling et al. |
| 2006/0276707 | A1 | 12/2006 | Ya'akov et al. |
| 2008/0191298 | A1 | 8/2008 | Lin et al. |
| 2008/0305753 | A1 | 12/2008 | Stark |
| 2009/0070922 | A1 | 3/2009 | Murata et al. |
| 2010/0134794 | A1 * | 6/2010 | Odegard ................ G01N 21/33 356/326 |
| 2012/0268618 | A1 | 10/2012 | Imai |
| 2015/0031049 | A1 | 1/2015 | Kentsis et al. |
| 2015/0167280 | A1 | 6/2015 | Le et al. |
| 2015/0320404 | A1 | 11/2015 | Kramer |
| 2017/0322197 | A1 * | 11/2017 | Hall .................... G01N 33/493 |

FOREIGN PATENT DOCUMENTS

| | | | |
|---|---|---|---|
| WO | 2009035599 A1 | 3/2009 | |
| WO | WO-2016135735 A1 * | 9/2016 | ......... A61B 10/0038 |

* cited by examiner

Transmitting radiation by one or more transmitters that may be attached to a toilet boil. 310

Receiving, by one or more sensors that may be attached to the toilet bowl, received radiation that passed through the urine sample. 320

Generating, by the one or more sensors, detection signals indicative of an intensity of the received radiation at multiple frequencies. 330

Participating, by processor, in the urine sample analysis for determining a content of the urine sample based on the detection signals. 340

Sensing, by a triggering sensor, a condition for triggering an activation of the one or more transmitters and the one or more sensors. 304

Activating the one or more transmitters and the one or more sensors. 306

Deactivating the one or more transmitters and the one or more sensors. 308

HOME TOILET SYSTEM FOR MONITORING URINE COMPONENTS IN REAL TIME WHILE URINATION

BACKGROUND

Urine Measurements

To this day, there is no system for measuring the composition of urine in real time without changing the way of urination.

Current solutions demand patients to urinate into a cap and then analyze in a clinical center, sticks, or other expensive instruments. The present invention will be cheap, in real time, available for daily testing, easy to use and will eliminate the needs for such elaborate processes.

Current solutions are used as a disease detection after the symptoms appear and after the doctor give a recommendation for a urine test. The present invention will provide an ongoing continuous basis screening of health conditions to prevent, in advance, the appearance of symptoms and enables the treatment in an early stage.

Currently, there is no universal spectral database of healthy and available urine for personal usage.

Baseline

Finding interesting molecules by spectroscopy requires measurements with and without the molecule. The concentration of these molecules is can be calculated from the gap between the two measurements. To achieve a satisfactory accuracy, the variance needs to be smaller than the difference between the background and the sampling spectrum.

Urine is a liquid containing up to 3000 different molecules. These molecules affect the absorption spectrum, so the spectral feature of urine can have high variability, which can exceed the signal of the molecule under interest.

For example, to this day, no method has been found to measure and calculate protein concentration in various urine sample using accurate, objective, and direct methods. The only way for this is by indirect methods that include adding chemical reagents, which color the urine according to the concentration of the molecule.

As a result, ordinary (known) direct methods do not calculate the concentration of molecules in different urine. Therefore, a method that eliminates the effect of background molecules is required.

SUMMARY

There may be provided systems, methods and computer readable medium as illustrated in the specification.

BRIEF DESCRIPTION OF THE DRAWINGS

The embodiments of the disclosure will be understood and appreciated more fully from the following detailed description, taken in conjunction with the drawings in which:

FIG. 15 illustrates an example of a method;

DESCRIPTION OF EXAMPLE EMBODIMENTS

Figure 1A:
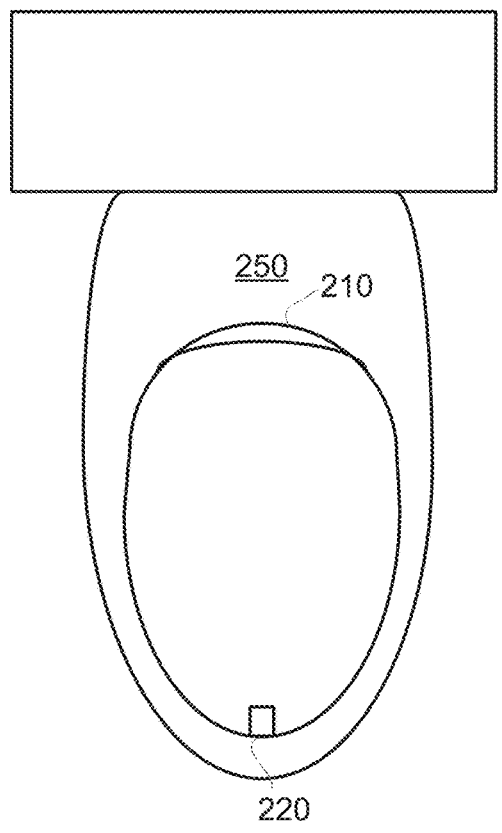
FIGS. 1A-1F 2-9, 10A, 10B, 11A, 11B, 12A-12E, 13A-13B, and 14A-14D illustrate examples of a system and a toilet.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

Because the illustrated embodiments of the present invention may for the most part, be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

Any reference in the specification to a method should be applied to mutatis mutandis to a device or system capable of executing the method and/or to a non-transitory computer readable medium that stores instructions for executing the method.

Any reference in the specification to a system or device should be applied mutatis mutandis to a method that may be executed by the system, and/or may be applied mutatis mutandis to non-transitory computer readable medium that stores instructions executable by the system.

Any reference in the specification to a non-transitory computer readable medium should be applied mutatis mutandis to a device or system capable of executing instructions stored in the non-transitory computer readable medium and/or may be applied mutatis mutandis to a method for executing the instructions.

Any combination of any module or unit listed in any of the figures, any part of the specification and/or any claims may be provided.

The specification and/or drawings may refer to a processor. The processor may be a processing circuitry. The processing circuitry may be implemented as a central processing unit (CPU), and/or one or more other integrated circuits such as application-specific integrated circuits (ASICs), field programmable gate arrays (FPGAs), full-custom integrated circuits, etc., or a combination of such integrated circuits.

Any combination of any steps of any method illustrated in the specification and/or drawings may be provided.

Any combination of any subject matter of any of claims may be provided.

Any combinations of systems, units, components, processors, sensors, illustrated in the specification and/or drawings may be provided. For example—any of the systems may include a power source, a processor, a controller, as well as one or more sensor and one or more transmitter.

Any value (for example wavelength, number of LEDs, field of view, angles, and the like), any configuration, system components and the like is merely a non-limiting example.

The application may refer to urine. It should be noted that any reference to a urine may be applied mutatis mutandis to any other freely moving fluid (freely—without having its propagation path and/or drop shape and size) known in advance and/or dictated by a conduit that forces one propagation path.

Urine Measurements

There may be provided a system for urine sample analysis, the system may include one or more transmitters for transmitting radiation; one or more sensors that may be configured to receive received radiation that passed through the urine sample and to generate detection signals indicative of an intensity of the received radiation at multiple frequencies; detaching elements that may be configured to detach the one or more transmitters and the one or more sensors to a toilet bowl; and a processor that may be configured to participate in the urine sample analysis for determining a content of the urine sample based on the detection signals.

The sample may include one or more drops of urine or any other sample.

The system may include a triggering sensor that may be configured to sense a condition for triggering an activation of the one or more transmitters and the one or more sensors.

The triggering sensor may be a proximity sensor that may be configured to sense a presence of a person within a proximity of the toilet bowl and generate a proximity alert.

The triggering sensor may be an acoustic sensor.

The triggering sensor may be a toilet cover motion sensor.

The triggering sensor may be configured to detect a start of a urination.

The system may include one or more additional triggering sensors to provide multiple triggering sensors for sense a condition for triggering an activation of the one or more transmitters and the one or more sensors.

The at least two triggering sensors sensor differ from each other by a type of sensed event.

The system may include a detaching element for detaching the triggering sensor to the toilet.

The detaching element may be configured to position the triggering sensor outside the toilet bowl.

The detaching element may be configured to position the triggering sensor inside the toilet bowl.

The one or more sensors may be multiple sensors.

The system, wherein at least two of the sensors have different fields of view.

The system wherein fields of view of the multiple sensors cover a majority of a virtual horizontal plane of an inner space defined by the toilet bowl. A majority—at least 51, 55, 60, 65, 70, 75, 80, 85, 90, 95 percent and the like.

The system, wherein at least two of the sensors have partially overlapping fields of view.

The multiple sensors form a curved one-dimensional array of sensors.

The multiple sensors may be spaced apart from each other.

The at least two of the sensors have different spectral responses.

The at least one sensor may be preceded by a spectral filter.

The at least one sensor may be preceded by a tunable spectral filter.

The system wherein at least some of the multiple sensors may be at least partially shielded by a rim of the toilet bowl.

The system wherein at least some of the multiple sensors extend outside a rim of the toilet bowl.

The processor may be configured to control an operation of at least some of the one or more transmitters and the one or more sensors.

The one or more transmitters may be multiple transmitters and wherein at least some of the multiple transmitters may be configured to transmit in a sequential manner.

The one or more transmitters may be multiple transmitters and wherein at least some of the multiple transmitters may be configured to transmit radiation of different frequencies at different points of time.

The one or more transmitters may be multiple transmitters and wherein at least some of the multiple transmitters may be configured to transmit in a partially overlapping manner.

The processor may be configured to participate in the urine analysis process by at least calculating attenuation values at the multiple frequencies.

The processor may be configured to participate in the urine analysis process by calculating attenuation values at the multiple frequencies and applying a machine learning process on the attenuation values to provide at least an initial estimation of the content of the urine sample.

The multiple frequencies may be discrete and space apart frequencies that exceed five frequencies.

The at least one of the transmitters transmits broadband radiation.

The system may include one or more power supply links coupled to the one or more transmitters and the one or more sensors.

The processor may be configured to ignore detection signals obtained at predefined ambient conditions.

The system may include one or more communication links for conveying the detection signals to the processor.

The system may include one or more batteries for supplying power to the one or more transmitters and to the one or more sensors.

The one or more sensors may be also configured to receive reference radiation that did not pass through the urine sample.

The multiple frequencies may include a first water absorbance frequency, second frequencies and a second water absorbance frequency; wherein (a) an absorbance of water to radiation of the first water absorbance frequency, and (b) an absorbance of water to radiation of the first water absorbance frequency may be known.

The system may include one or more reflecting elements for reflecting the radiation towards the one or more sensors.

There is provided a system that enables personal and frequent monitoring/screening urine in free style. For example, a daily protein test for pregnant women (Preeclampsia), without sticks and without changing urination habits. Other interesting test are blood in urine for kidney condition, ketone to test hydration, nitrites as indication for bladder infection, etc.

The system is configured to be installed in any toilet at any location for example above the splash water level (about the size of a cigarette package) without touching/collecting the urine and the waste water inside the toilet—or below the splash water level.

The system is configured to be able to measure the spectral information of the urine in motion. The spectrum measures by dividing the light to its spectral components. For example, this can be done by using a grating spectrometer or other type of spectrometer, by using tunable filters (e.g. Fabry Perot resonator), filter array, LEDs array, lasers, filter wheel, etc.

The system may include an illumination part, a collection and sensing part, processing part, communication unit, and a power unit.

The parts are placed into the toilet one in front the other or in the same side with or without a mirror in front of them—or in any spatial relationship as long as one or more sensors of the collection and sensing part may sense radiation emitted by the illumination part that passed through or reflected from the urine.

In various figures at least the illumination path was installed at a rear part of the toilet bowl—it should be noted that any part of the system may be installed at any part of the toilet bowl—and any angle in relation to a longitudinal axis of the toilet (that in FIG. 1 crosses the LEDs array and the photodiodes array).

The installation can be done in any manner using any attachment means (glue, mechanical elements, fixed to the toilet, removable from the toilet, and the like).

The illumination part, a collection and sensing part may operate in one or more frequencies and/or one or more frequency ranges and may include optical components such as one or more LEDs, lamps, any other radiation source, one or more sensors of any type, one or more filters, one or more polarizers, one or more analyzers, and the like.

The processing part may include one or more processors, one or more memory units, and the like.

The one or more memory units may store measurements, for at least a period required for obtaining and transmitting the measurements. The one or more memory units may be any type of memory units-volatile, non-volatile, FIFOs, queues, and the like.

The system may include a user identifier or may be configured to communicate with a user identifier for identifying a user that is urinating and associating the detection signals with that user. Non-limiting examples of user identifiers may include a smartphone Bluetooth, a real button, voice recognition, a Bluetooth button, image facial recognition system, fingerprint, wearable devices or any other NFC device that may transmit or otherwise provide a user identifier.

The identification of the user may be done based on the urine provided by the user.

The communication unit may be configured to output detection signals or any other data or metadata generated by the system. The communication unit may be a wireless communication unit, a wired communication unit and the like. For example—it may include a transmitter (Bluetooth, WiFi and the like) that may transmit the data directly or indirectly (for example to a user device such as a mobile phone that may further output this) to a computerized system such as a cloud computerized system that may access a dedicated database.

The system itself may perform at least some of the processing of the detection signals generated by the one or more sensors.

The parts of the system may include a power source or may be fed by a power source such as a battery, and/or a wired power cable connected to a power supply port near the toilet.

The system may include a power management unit that may activate the system upon a detection of a trigger and following the measurement (for example when not receiving samples of radiation passing through the urine and/or after a certain time period lapsed from the activation) may deactivate the system. The system may be activated for a predefined time after activation (for example 3, 5, 10, 15, 20, 30, 45 second and the like) and then enter idle mode—for power reduction.

The power management system may perform automating system switching (activation and/or deactivation) using one or more sensors (triggering sensors) such as sonar, volume, voice recognition, or any other proximity detection system such as a RFID device (bracelet, NFC).

The system may include at least one additional sensor or may obtain information from at least one additional sensor. Additionally, or alternatively, a processing of the detection samples (by the system or the computerized system) may take into account information from at least one additional sensor.

The least one additional sensor may be, for example at least one other sensor such as a temperature sensor, a humidity sensor, and the like for providing more information regarding the environment of the toilet and/or the urine itself.

For example—it may be beneficial to measure urine of certain temperatures and ignore urine of other temperatures (for example ignore measurements of urine below 30 degrees Celsius).

At least one additional sensor may provide geographical information such as the weather outdoors, season of the year and other geo specific information.

In various examples that system may include one or more light sources (such as LEDs, halogen bulbs, xenon lamps, lasers), one or more sensor (such as photodiodes, spectrometer, 2D detector, camera) and other optical components (such as lenses, mirrors, filters, tunable sensors such as Fabry-Perot resonator, etc.) the system measures the spectral characterization (UV, VIS, NIR, SWIR, MIR, LIR, or other) of the urine in motion.

The system may include optical components (such as lenses, mirrors, polarizers, etc.) to focus the signal on one or several sensors and/or a perform any other optical manipulation of change of direction, polarization, collimation, and the like.

The following examples are non-limiting examples for various configurations of a system.

The illumination part may include one or more arrays of LEDs that covers part of the spectral range between 350-2500 nm (with a spectral FWHM of 10 nm to 200 nm) that can provide detection for the selected molecules. For example, protein 1070-1900 nm, RBC 400-700 nm, etc.

The LED's viewing angle may be, for example, between 5 deg and 60 deg in order to cover all toilet space. The viewing angle may depend upon the number and arrangement of the LEDs.

It is possible to focus the system on three LEDs at wavelengths of 1450 nm, 1350 nm, and 1650 nm if base lining can be performed externally to the spectral range indicated. Yet another example—wavelengths of 1070, 1450, 1900 nm.

The system may include a single LEDs array which include all the selected LEDs (one or more from each) and one photodiodes array that include Photodiodes that cover the LEDs spectral range (one or more from each). The LEDs and Photodiodes may be arranged in a way that transmitted/reflected LEDs radiation from urine is measured by the appropriate Photodiodes, this can be in different way (one row/column, as a 2D array, freestyle).

The system may include an array(s) of Photodiode that covers the spectral range of the selected LEDs. The array(s) need to be able to collect the transmitting/reflected light from all light sources from urine.

The system may generate detection samples at one or more sampling rate.

The lowest sampling rate should be high enough to sample the falling urine. The speed of fall can be calculated by the falling drop of water in a gravity field (constant acceleration).

$$V = \sqrt{2gh} = \sqrt{10}\left[\frac{m}{\sec}\right]; g = 10\left[\frac{m}{\sec^2}\right], h = 0.5[m]$$

The sampling rate should be fast enough to show a drop characterization (shape).

For example—the inventor used a sampling rate of 3 kHz, 100 kHz, 500 kHz and the like. Other sampling rates may be applied.

The system may be operated in various manner. An example of an operation of the system is listed below:

The system activates each time a different LED for a period of time. Each LED is active for a period of time that gives the possibility to measure at least one drop shape.

One or more photodiodes (or any other sensors) records the voltage as a response of the light.

This process is repeated to all LEDs during the urination time or until a stop message is received from the processor or from any other source communicating with the LEDs.

The detection signals generated by the one or more photodiodes are collected and sent for analysis—by a processing circuit of the system, by another computer, by a remote computer, and the like The analysis will give indication about different molecules presented in the urine, such: protein, RBC, WBC, ketone, nitrite, etc.

The analysis can give indication about presence of alcohol or drugs in the urine.

The analysis can give information about physical properties such as volume, pressure, speed, frequency, position, color, etc.

The stored measurement signals may include reference measurement signals (at the absence of illumination by the system) and measurement signals when the toilet with/without the urine is illuminated.

The number of LEDs in the array and/or number of photodiodes in the array may vary (up to a number that covers the toilet area and provides information from the urine).

The one or more light sources may be Broadband light sources (halogen bulbs, xenon, etc.), and a tunable filter (such as tunable Fabry-Perot resonator) or statice optical filters.

There may be any spatial relationship between one or more transmitter and one or more sensors. For example—a sensor and a transmitter may be of the same height within the toilet bowl or may be at different heights and/or a sensor and a transmitter may face each other or may be oriented to each other (for example having optical axis that are not parallel to each other).

There may be any number of sensors and/or any number of transmitters.

A sensor may include single sensing element of multiple sensing elements. Different sensing elements may have the same spectral response or may differ from each other by their spectral response. Different sensing elements may have the same sensitivity or may differ from each other by their sensitivity.

Any reference to a sensor, an array of sensors, a transmitter, an array of transmitters, a filter or any other optical and/or mechanical and/or computerized element should be applied mutatis mutandis to multiple sensors, multiple arrays of sensors, multiple transmitters, multiple arrays of transmitters, multiple filters or any other multiple optical and/or mechanical and/or computerized elements, respectively.

Any reference to a type of a sensor, an array of sensors, a transmitter, a filter or any other optical and/or mechanical and/or computerized element should be applied mutatis mutandis to any other type of sensor, array of sensors, transmitter, filter or any other optical and/or mechanical and/or computerized element respectively.

Any sensor, array or sensors, transmitter, array of transmitters, filter, any other optical and/or mechanical and/or computerized element may be located at locations that differ from those illustrated in the figures.

Any reference to a processor may be applied mutatis mutandis to a controller.

FIG. 1A illustrates a system that includes transmitter 210 and a sensor 220 that face each other—for example the transmitter 210 located at the rear part of the toilet bowl while the sensor 220 is located at the front part of the toilet bowl.

In relation to any of the figures—the sensor and the transmitter can be located at any other locations.

Figure 1B:
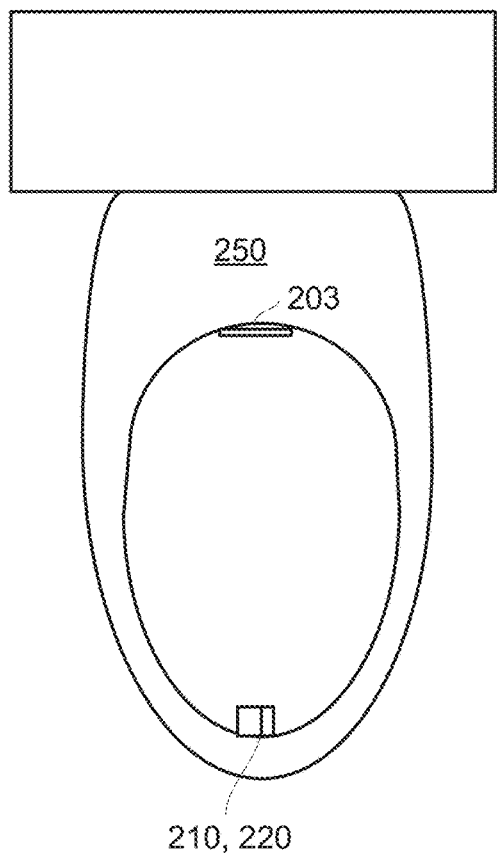

FIG. 1B illustrates a system that includes transmitter 210 and a sensor 220 located at the same side and a mirror 203 faces the sensor and the transmitter—so that the mirror reflects radiation that passes through a urine sample to pass again through the urine and impinge on the sensor.

Figure 1C:
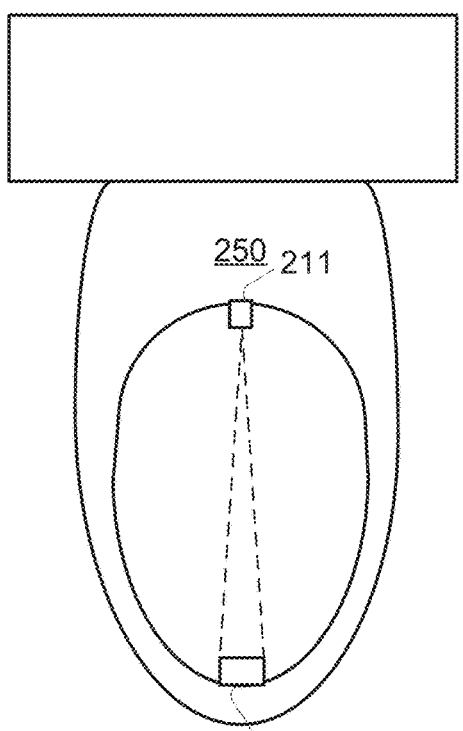

FIG. 1C illustrates a system that includes transmitter such as LED array 211 and a sensor such as a photodiode array 221 that face each other.

Figure 1D:
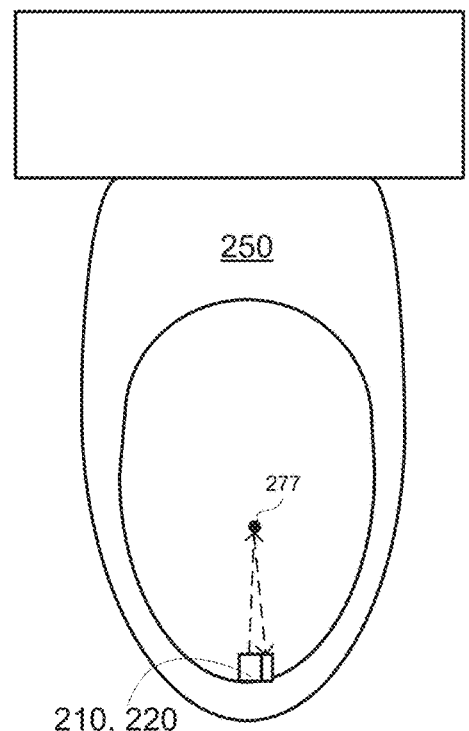

FIG. 1D illustrates a transmitter 210 and a sensor 220 located at the same side of the toilet bowl—as the sensor is aimed to detect radiation reflected from the urine sample (denoted by spot 277).

Figure 1E:
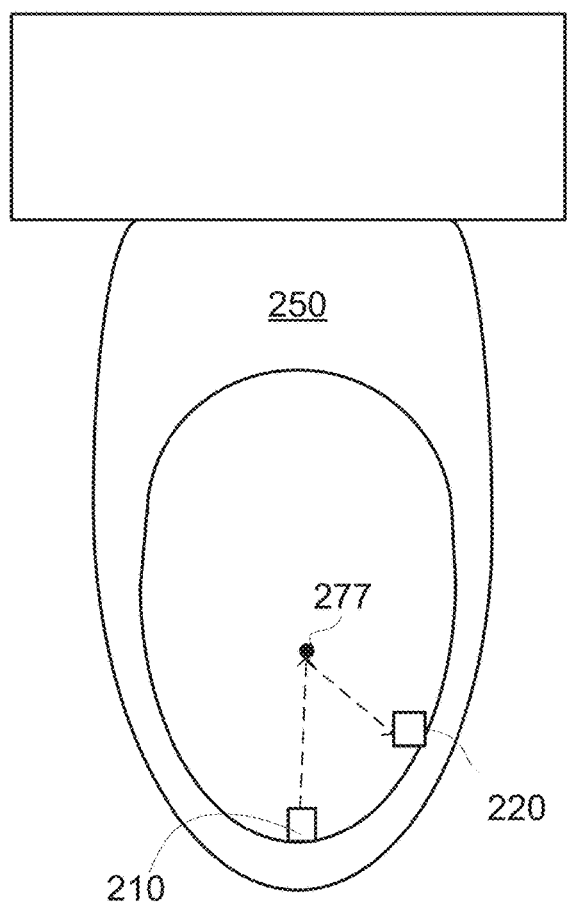

FIG. 1E illustrates a transmitter 210 and a sensor 220 located at a certain angle to the right of the transmitter—to receive radiation reflected to the side of the urine sample (denoted by spot 277).

Figure 1F:
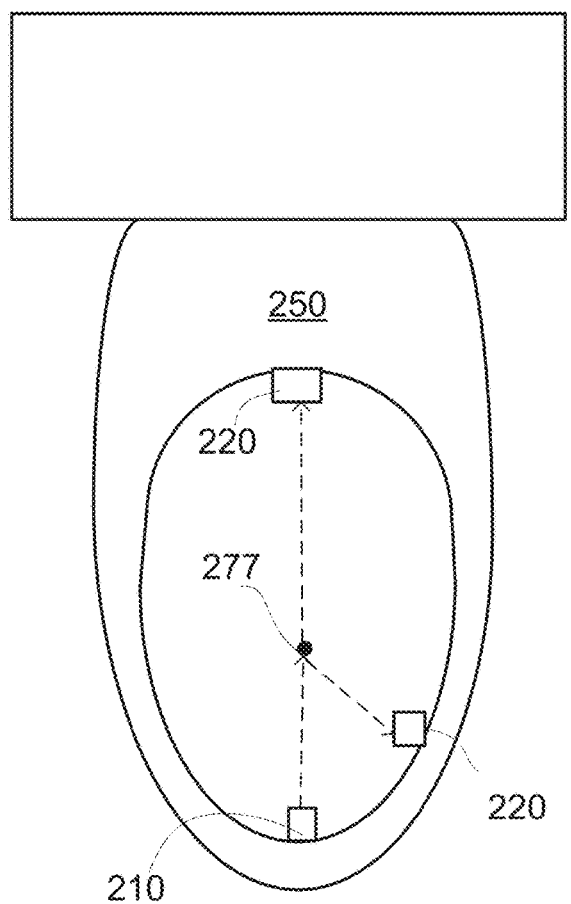

FIG. 1F illustrates a transmitter 210 and two sensors—one of the sensor 220 is located at the opposite side of the toilet bowl and a second sensor located at a certain angle to the right of the transmitter—to receive radiation reflected to the side of the urine sample (denoted by spot 277).

Figure 2:
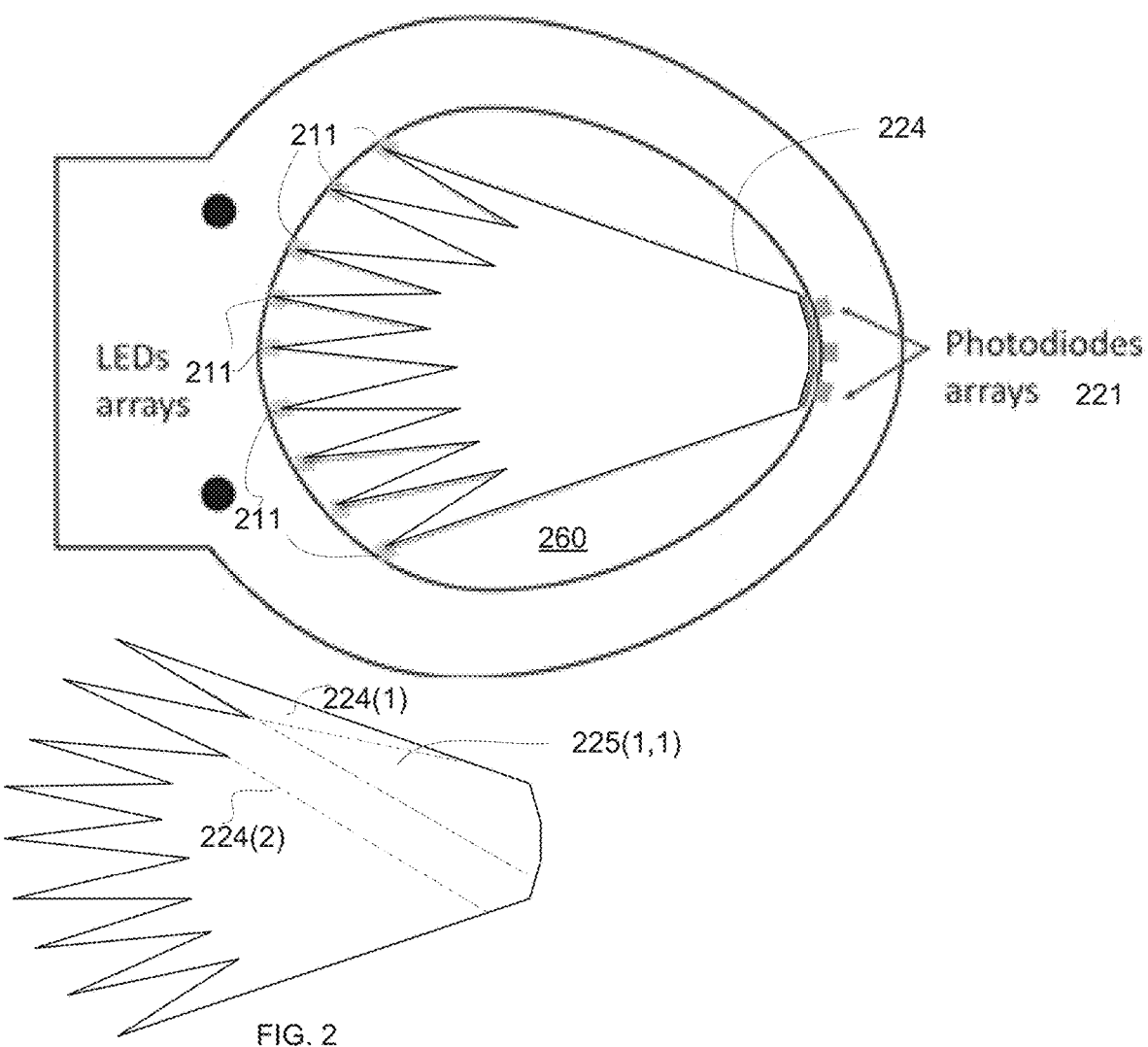

FIG. 2 illustrates several LED arrays 211 positioned at different angles installed at the rear part of the toilet bowl and a number of photodiode arrays 221 located at the front part of the toilet bowl. The figure also illustrates the aggregate 224 field of view 250 of the different LED array—it covers a majority of a virtual horizontal plane 260 of an inner space defined by the toilet bowl. The aggregate field of view includes fields of views of different LED arrays—such as first field of view 224(1) and second field of view 224(2) that have an overlap area 225(1,2).

Figure 3:
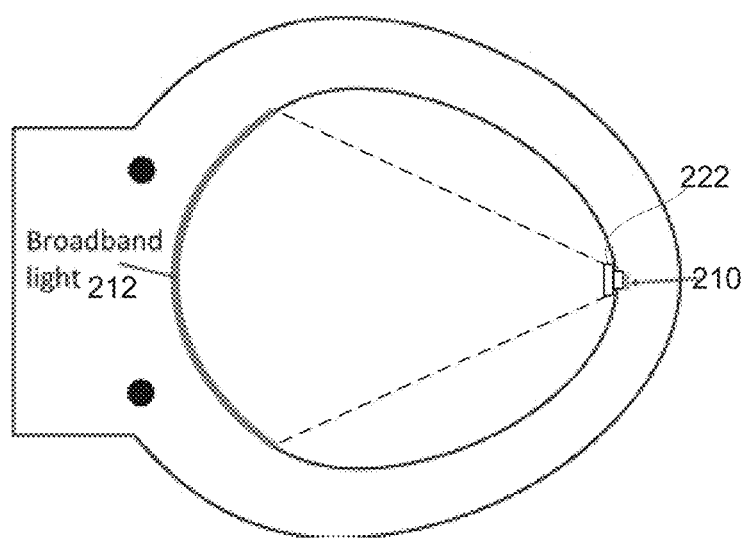

FIG. 3 illustrates a broadband light source 212 that is curved and is installed at the rear part of the toilet bowl and a Fabry Perot resonator 222 followed by a sensor 210 located at the front part of the toilet bowl.

Broadband—may be while light or a frequency range that exceeds 300, 400, 500, 600, 700, 800 nanometers.

Figure 4:
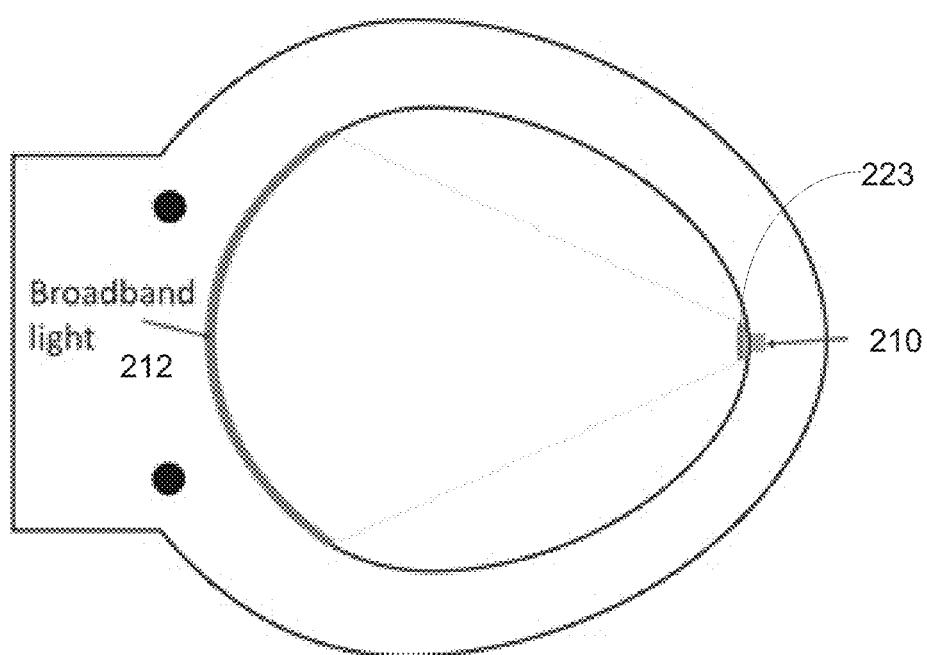

FIG. 4 illustrates a broadband light source 212 that is curved and is installed at the rear part of the toilet bowl and a tunable filter 223 followed by a sensor 210 located at the front part of the toilet bowl.

Figure 5:
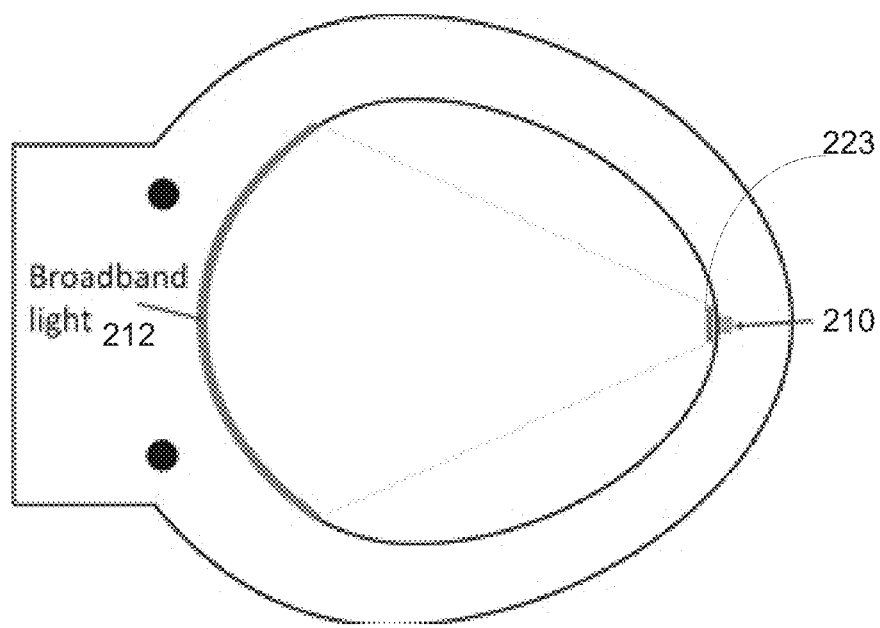

FIG. 5 illustrates a broadband light source 212 that is curved and is installed at the rear part of the toilet bowl and a filter array 223 that precedes one or more sensors 210 located at the front part of the toilet bowl.

Figure 6:
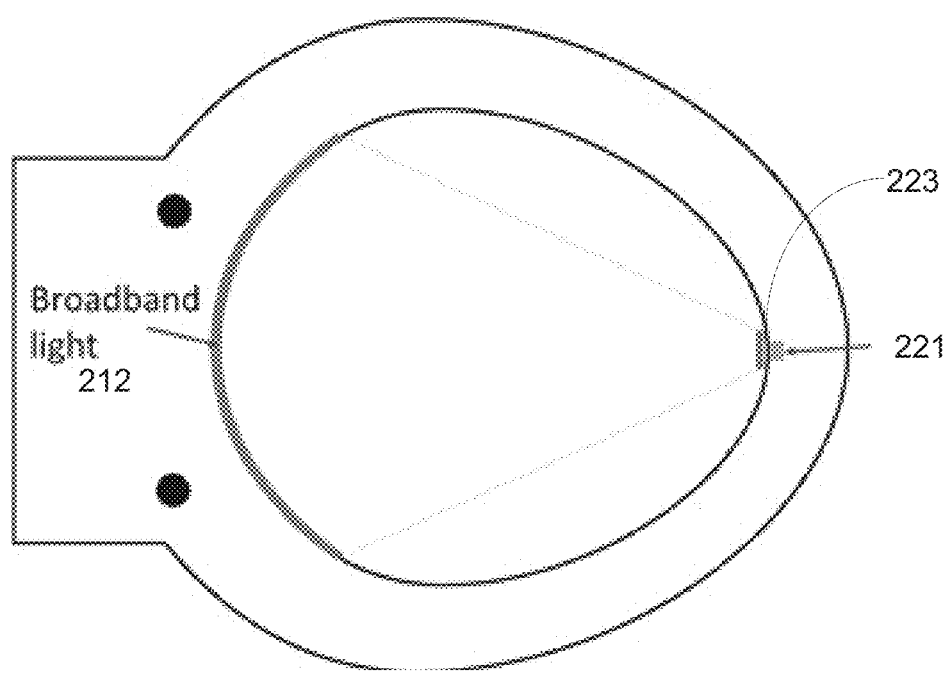

FIG. 6 illustrates a broadband light source 212 that is curved and is installed at the rear part of the toilet bowl and a filter 223 and photodiode array 221 located at the front part of the toilet bowl.

Figure 7:
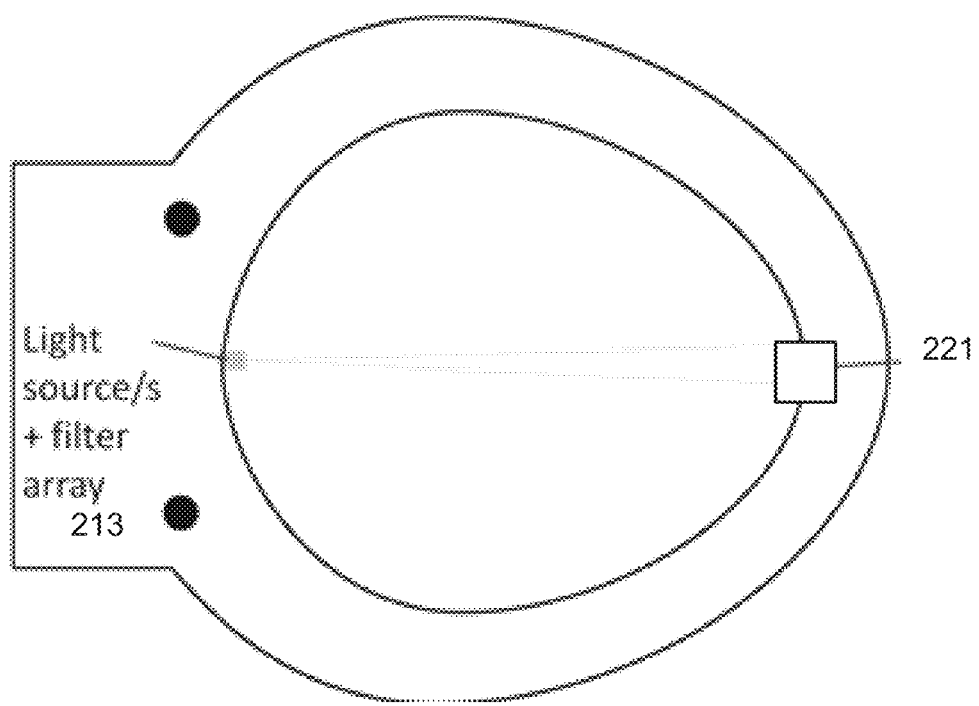

FIG. 7 illustrates one or more light sources and a filter array (collectively denoted 213) that are installed at the rear part of the toilet bowl and a photodiode array 221 located at the front part of the toilet bowl.

Figure 8:
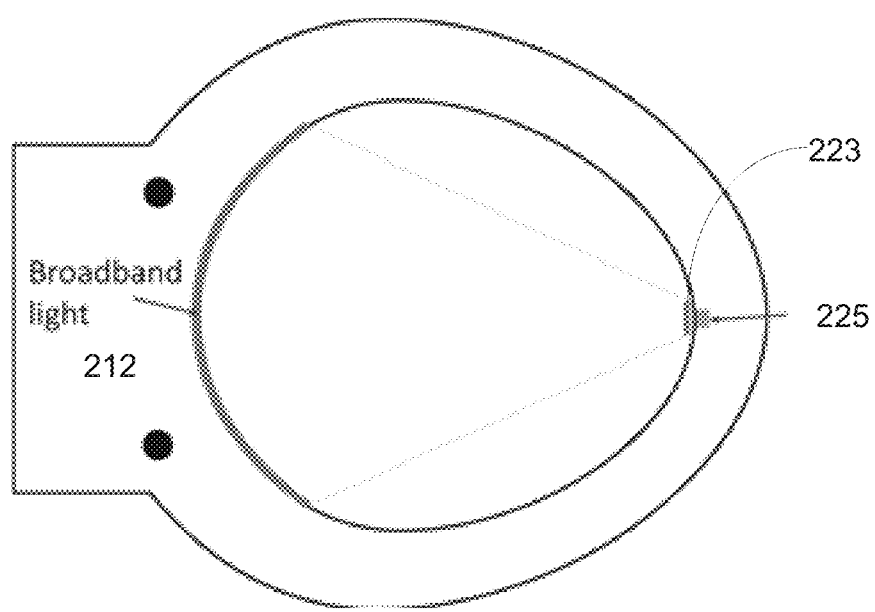

FIG. 8 illustrates a broadband light source 212 that is curved and is installed at the rear part of the toilet bowl and a spectrometer 225 located at the front part of the toilet bowl.

Figure 9:
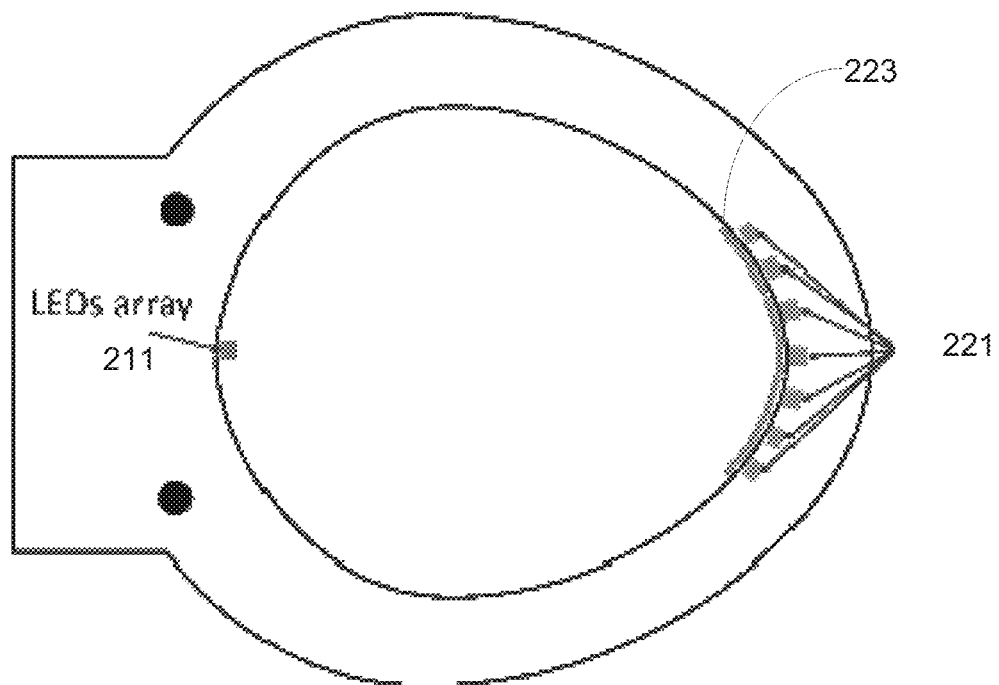

FIG. 9 illustrates LED arrays 211 installed at the rear part of the toilet bowl and photodiode arrays 221 distributed along an angular range and preceded by an array of filters 223 located at the front part of the toilet bowl.

Figure 10A:
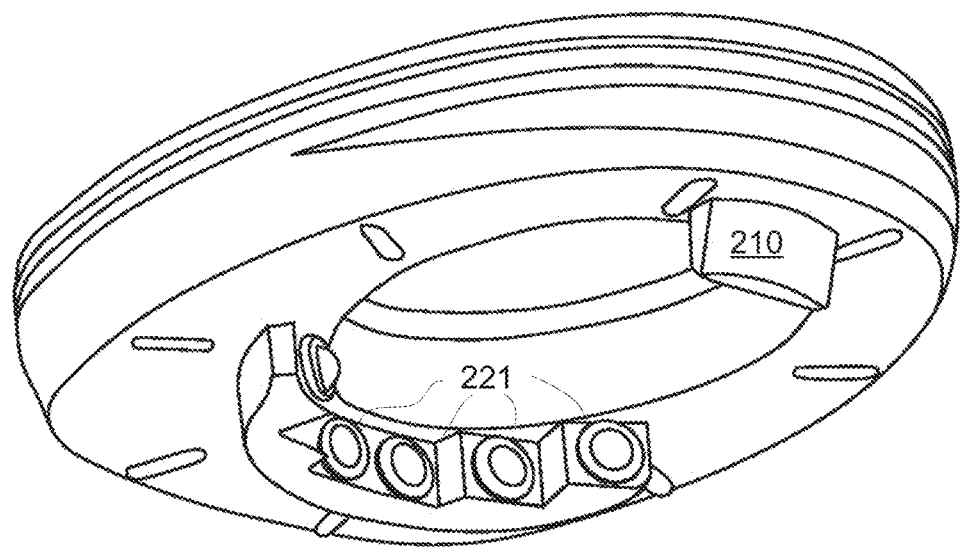
Figure 10B:
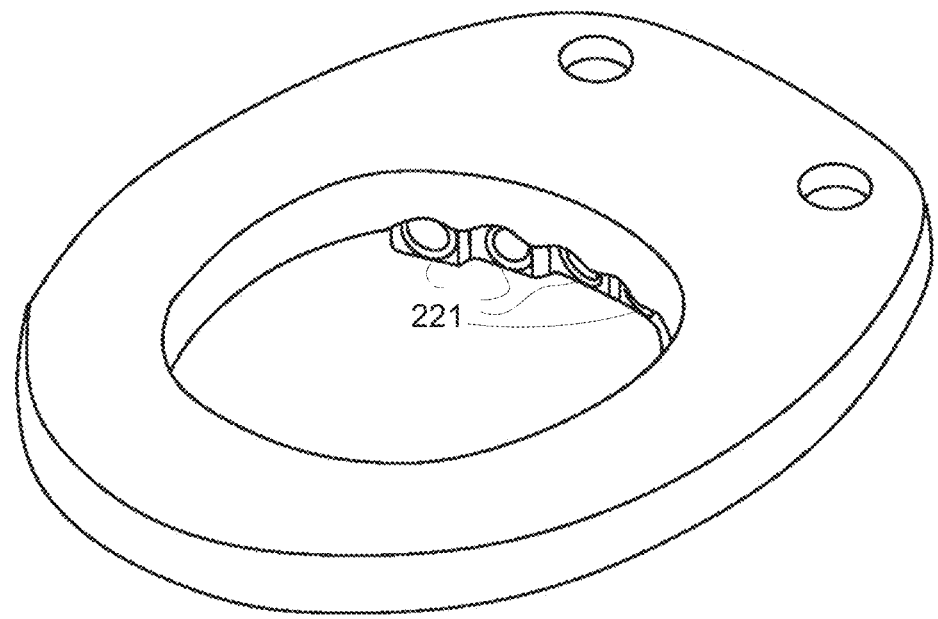

FIGS. 10A and 10B illustrate a system that includes transmitter 210 located at the front part of the toilet bowl while photodiode arrays 221 are located at the rear part of the toilet bowl.

Figure 11A:
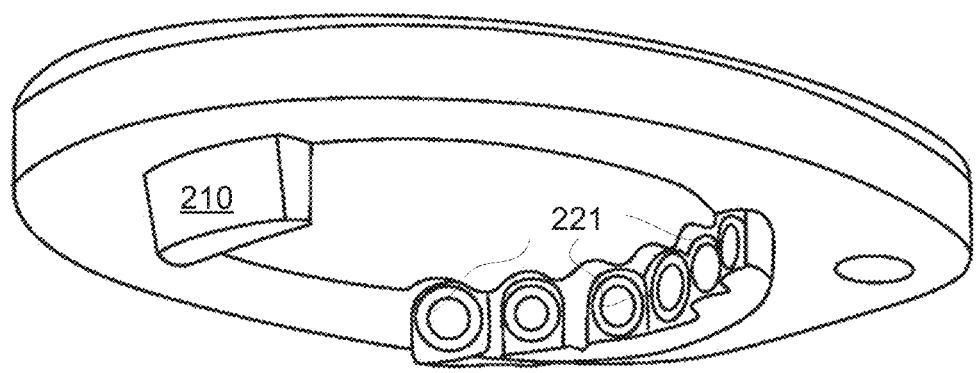
Figure 11B:
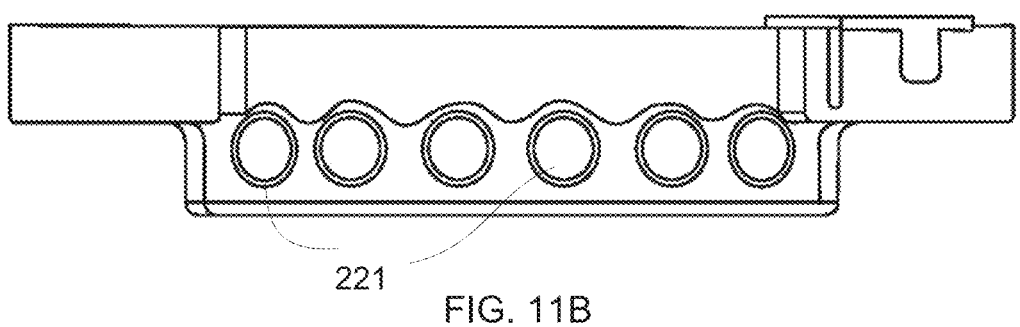

FIGS. 11A and 11B illustrate a system that includes transmitter 210 located at the front part of the toilet bowl while photodiode arrays 221 are located at the rear part of the toilet bowl.

Figure 12A:
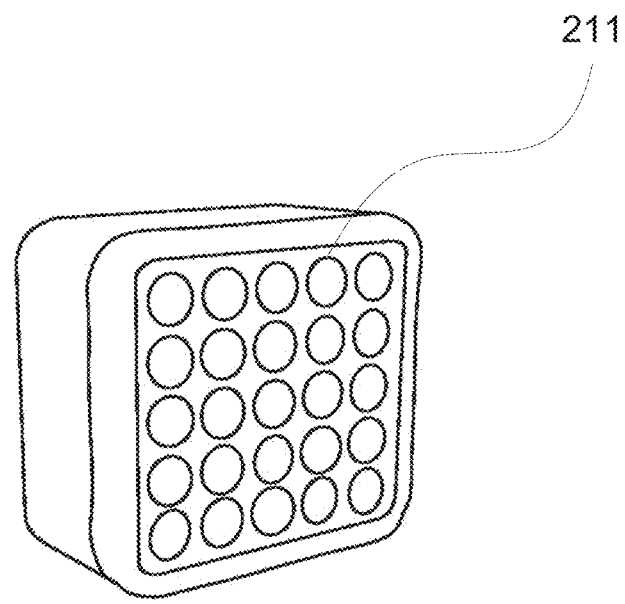
Figure 12B:
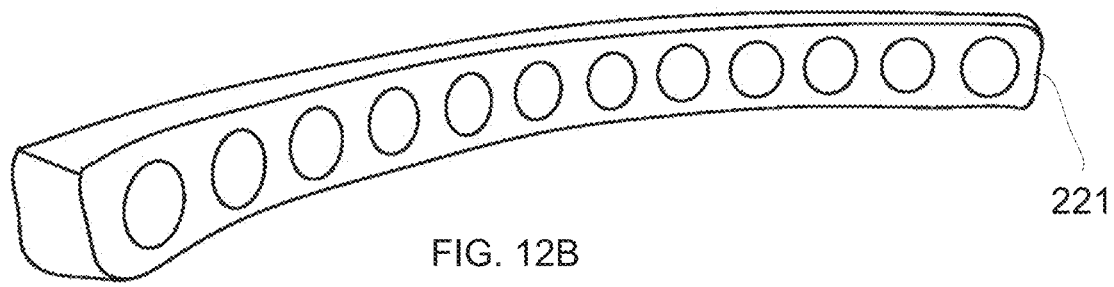
Figure 12C:
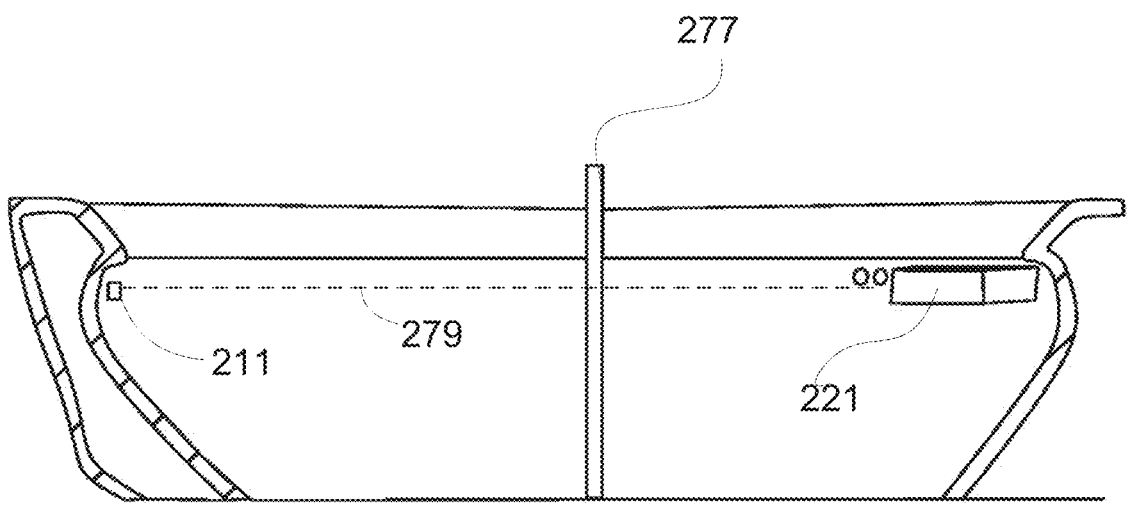
Figure 12D:
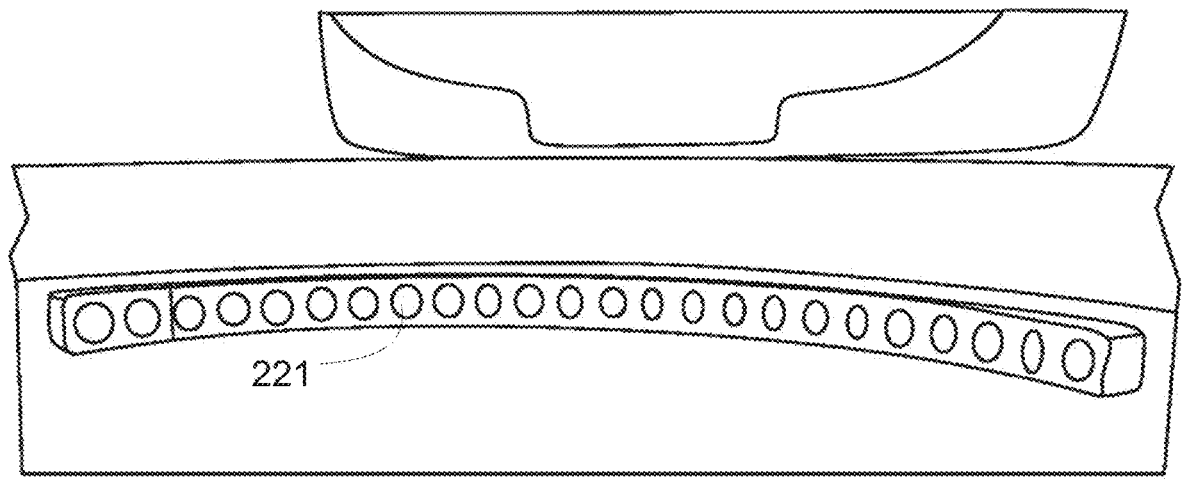
Figure 12E:
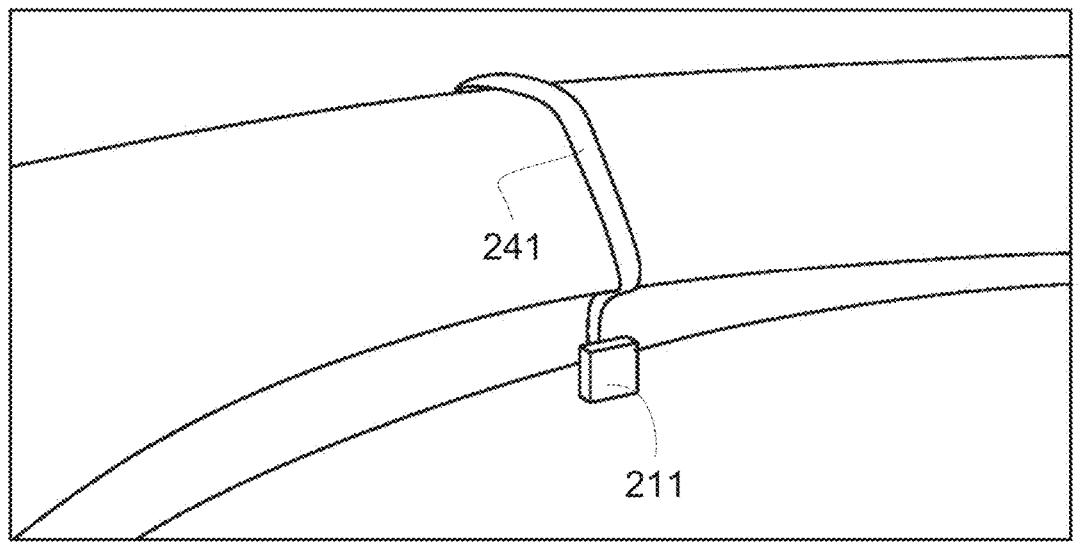

FIGS. 12A, 12B, 12C, 12D and 12E illustrate a system that includes LED array 211 located at the front part of the toilet bowl while photodiode arrays 221 are located at the rear part of the toilet bowl. These figures also illustrate a detachment element 241. FIG. 12C also shows radiation 279 that is transmitted by LED array 211 and passes through urine sample 277 to provide attenuated radiation that reaches photodiode arrays 221.

Figure 13A:
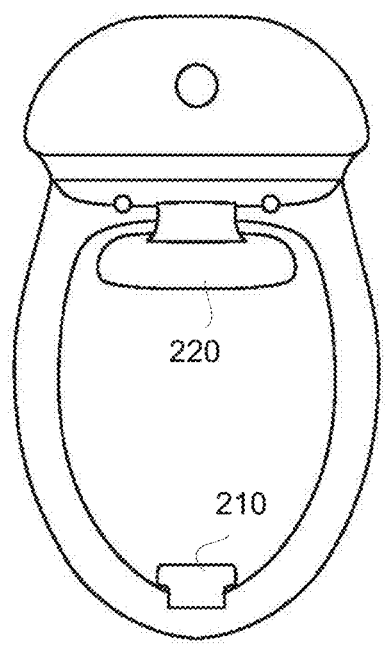
Figure 13B:
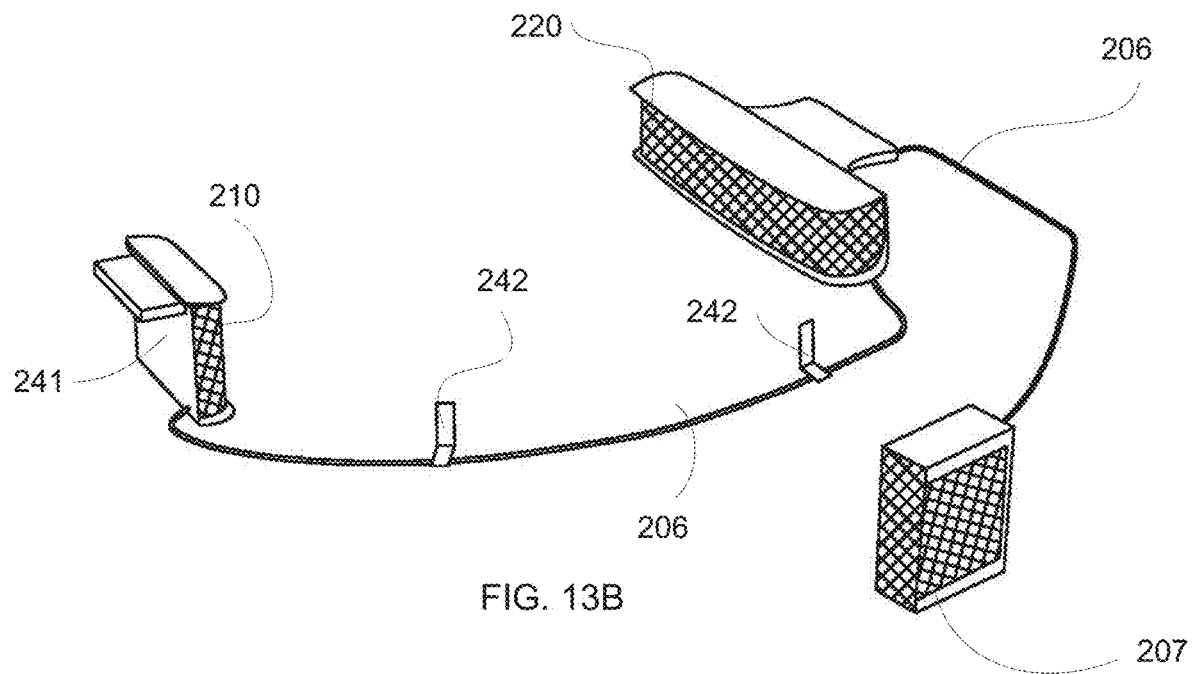

FIGS. 13A and 13B illustrate a system that includes sensors 220 located at the rear part of the toilet bowl while transmitter 210 is located at the front part of the toilet bowl. These figures also illustrate links 206 such as power and/or communication links, and a unit 207 that includes a processor and a power supply unit. The figures also illustrate additional detachment elements 242.

Figure 14A:
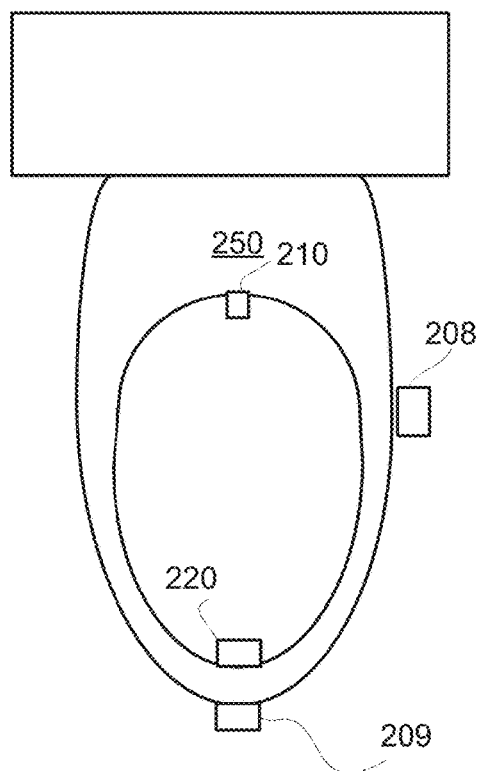

FIG. 14A illustrates a system that includes transmitter 210 and a sensor 220 that face each other, as well a processor 208 and triggering sensor 209 that is located outside the toilet bowl.

Figure 14B:
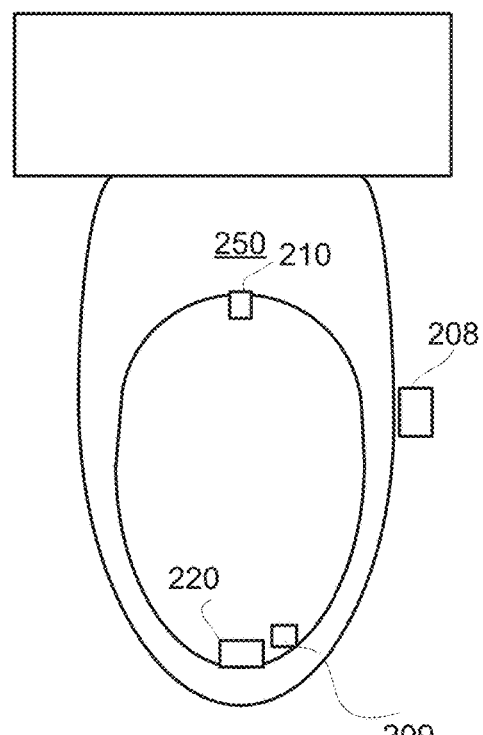

FIG. 14B illustrates a system that includes transmitter 210 and a sensor 220 that face each other, as well a processor 208 and triggering sensor 209 that is located within the toilet bowl.

Figure 14C:
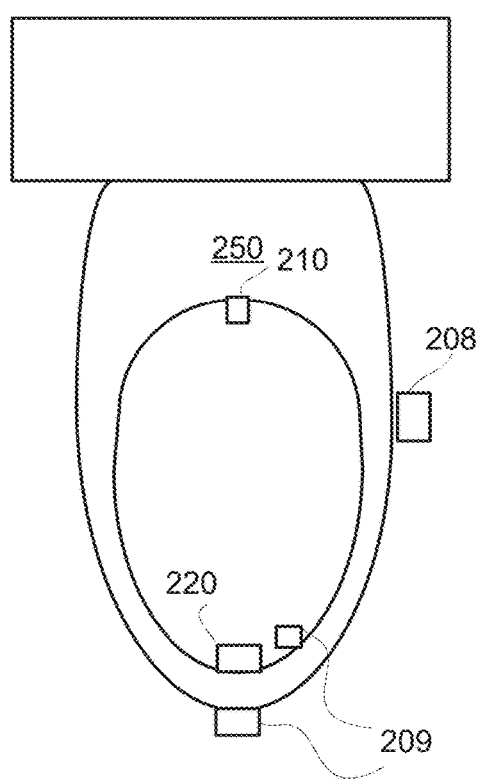

FIG. 14C illustrates a system that includes transmitter 210 and a sensor 220 that face each other, as well a processor 208 and triggering sensors 209—one located outside the toilet bowl and the other that is located within the toilet bowl.

Figure 14D:
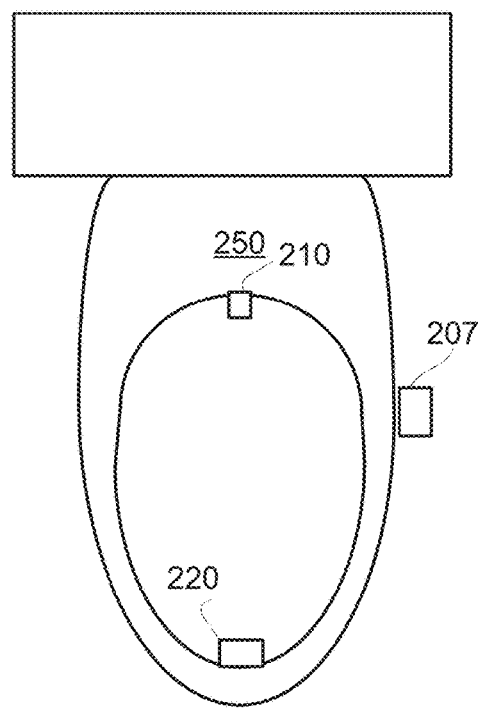

FIG. 14D illustrates a system that includes transmitter 210 and a sensor 220 that face each other, as well a unit 207 that includes a processor and a supply unit and may also include a triggering sensor.

FIG. 15 illustrates method 300. Method 300 may be executed by any of the systems illustrated in any of the previous figures.

Method 300 is for urine sample analysis and may start by step 310 of transmitting radiation by one or more transmitters that may be attached to a toilet boil.

Step 310 may be followed by step 320 of receiving, by one or more sensors that may be attached to the toilet bowl, received radiation that passed through the urine sample.

Step 310 may include transmitting radiation at the multiple frequencies.

Step 310 may include transmitting radiation at the multiple frequencies and at additional frequencies but filtering the additional frequencies before reaching the one or more sensors.

Step 310 may include transmitting, by at least some of the multiple transmitters in a sequential manner.

Step 310 may include transmitting, by at least some of the multiple transmitters radiation of different frequencies at different points of time.

Step 310 may include transmitting, by at least some of the multiple transmitters, in a partially overlapping manner.

Step 310 may be followed by step 320 of receiving, by one or more sensors that may be attached to the toilet bowl, received radiation that passed through the urine sample.

The received radiation may or may not be filtered before reaching the one or more sensors.

The received radiation may be reflected before reaching the one or more sensors.

The multiple frequencies may include a first water absorbance frequency, second frequencies and a second water absorbance frequency; wherein (a) an absorbance of water to radiation of the first water absorbance frequency, and (b) an absorbance of water to radiation of the first water absorbance frequency may be known.

Step 320 may include receiving the multiple frequencies simultaneously or sequentially—or a combination of both (receiving some of the multiple frequencies simultaneously).

Step 320 may be followed by step 330 of generating, by the one or more sensors, detection signals indicative of an intensity of the received radiation at multiple frequencies. The sensor may be any of the mentioned above sensors. The sensor may be radiation sensors, radiation sensors preceded by filters, and the like.

Step 330 may be followed by step 340 of participating, by processor, in the urine sample analysis for determining a content of the urine sample based on the detection signals.

The participating include performing at least one processing operation out of multiple processing operations that are included in the analysis.

One or more sequences of steps 310, 320 and 330 may be executed without having the radiation pass through the urine sample—this may provide reference information that may be used to determine illumination conditions—especially the signals sensed by the one or more sensors at the absence of urine—this may provide an indication about a non-attenuated (by urine) value of the radiation at the multiple frequencies.

Method 300 may include step 304 of sensing, by a triggering sensor, a condition for triggering an activation of the one or more transmitters and the one or more sensors.

Step 304 may be followed by step 306 of activating the one or more transmitters and the one or more sensors. After the completion of steps 310, 320 and, 330 the one or more sensors and the one or more transmitters can be deactivated (step 308)—which saves energy.

The triggering sensor may be a proximity sensor and step 304 may include sensing a presence of a person within a proximity of the toilet bowl.

The triggering sensor may be an acoustic sensor.

The triggering sensor may be a toilet cover motion sensor.

Step 304 may include detecting a start of a urination. This can be sensed by using an acoustic sensor, a vibration sensor that sensed the fluid within the toilet bowl, and the like.

In order to increase the reliability of step 304—step 304 may be executed by multiple triggering sensors—for example an acoustic sensor and a proximity sensor.

Method 300 may include an installment step of triggering sensor to the toilet. This may include positioning the triggering sensor outside the toilet bowl, positioning the triggering sensor inside the toilet bowl, or positioning any sensor and/or transmitter and/or controller or any other component/unit of the system.

The one or more sensors may be multiple sensors.

At least two of the sensors may have different fields of view.

The fields of view of the multiple sensors cover a majority of a virtual horizontal plane of an inner space defined by the toilet bowl.

At least two of the sensors may have partially overlapping fields of views.

The multiple sensors may form a curved one-dimensional array of sensors.

The multiple sensors may be spaced apart from each other.

At least two of the sensors may have different spectral responses.

At least one sensor may be preceded by a spectral filter.

At least one sensor may be preceded by a tunable spectral filter.

At least some of the multiple sensors may be at least partially shielded by a rim of the toilet bowl. Shielded may mean that at least a part of the multiple sensor does not extend outside the rim of the toilet bowl.

At least some of the multiple sensors extend outside a rim of the toilet bowl.

Method 300 may include controlling, by the processor, an operation of at least some of the one or more transmitters and the one or more sensors.

Step 340 may include calculating, by the processor, attenuation values at the multiple frequencies.

Step 340 may include calculating, by the processor, attenuation values at the multiple frequencies and applying, by the processor, a machine learning process on the attenuation values to provide at least an initial estimation of the content of the urine sample.

The multiple frequencies may be discrete and space apart frequencies that exceed five frequencies.

Step 310 may include transmitting, by at least one of the one or more transmitters, broadband radiation.

Method 300 may include at least one out of:

Supplying power by one or more power supply links coupled to the one or more transmitters and the one or more sensors. Method 300 may include detaching at least some of the one or more power supply links to a rim of the toilet boil.

Conveying detection signals over one or more communication links to the processor.

Supplying power, by one or more batteries, to the one or more transmitters and to the one or more sensors.

The method may include reflecting, by one or more reflecting elements, at least one of the radiation and reflected radiation towards the one or more sensors.

A urine sample may include one or more drops. Any reference to urine may be applied mutatis mutandis to another liquid—for example a liquid that may exhibits propagation property ambiguity (for example—location, pressure, drop size and/or size that may be unknown when a measurement occurs) within a space covered by the system. Any reference to a toilet bawl may applied, mutatis mutandis, to any other unit in which fluid may pass while exhibiting propagation property ambiguity.\

Any of the systems mentioned above may execute any of the steps illustrated below. Baseline may be calculated by systems that differ from any of the systems mentioned above.

Baseline

There is provided a method, system and a non-transitory computer readable medium for finding the presence and/or concentration of a molecule of interest in urine by applying a baseline algorithm. The urine samples may be taken from different people of different gender and/or different color and/or of different age, at different times, at different salinity and/or different acidity, and/under different medicinal conditions, and may applied without prior reference urine samples from these people.

The applying of the baseline algorithm may be included in a normalizing and stretching process. The process of normalization and stretching provides a framework for transforming values of any array into a common topographic map. Normalization transforms values to the [0:1] range. Stretching allows transformation of values to more complex and general cases by both linear and nonlinear functions.

The normalizing uses attenuation values obtained at first and second water reference frequencies in which the attenuation may be solely or almost solely dependent on water and not dependent on other elements of the urine. Stretching uses nonlinear functions formulating the interaction between molecules.

These reference frequencies and using test samples of urine in which concentrations of certain molecules were changed (for example increased) may provide various benefits—such as detecting molecules within combinations of many molecules within urine.

When performing spectral analysis of urine in any way optical/acoustic/electromagnetic the presence of other molecules does play a big role as overtones can mask each other, erase each other or increase each other. The suggested solution—including the normalization and using test samples of known content solves this problem. The interactions between molecules and their environment (such as electrically polar fields) are treated by nonlinear stretching (for example, quadratic).

The learning may use a supervised machine learning or an unsupervised machine learning process.

Most of the urine is water (for example up to 95 percent) and thus the most dominant absorption is water absorption.

The method may obtaining a set of detection signals of radiation that passes through a urine sample, the detection signals are associated with a group of radiation frequencies.

The detection signals include first detection signals associated with first frequencies (anchor or reference frequencies) and second detection signals associated with second frequencies.

The first frequencies are associated with predefined frequencies such as but not limited to (a) a maximal absorbance frequency of wafer (for example about 1900 nanometers) in which the water has minimal absorbance of radiation, and (b) a minimal absorbance frequency of wafer (for example about 1070 nanometers) in which the water has maximal absorbance of radiation.

Other first frequencies may be selected, such as 940 nanometer, 850 nanometer

The second detection signals are associated with second frequencies other than the first frequencies.

The number of different frequencies of the set may include a few frequencies, about nine frequencies, ten frequencies, a few tens of frequencies, or more than a few tens of frequencies.

A desired frequency of the set may be obtained by applying any one out of controlling the frequency of the emitted radiation (for example using radiation sources of certain frequencies and/or using filters), and/or controlling the frequency of the collection path (using filters, and/or using optics of certain frequency ranges, and/or using sensors that are sensitive to certain frequencies).

A detection signal of the set may represent a detection radiation in a frequency band of any width.

Before any calculation on the measured signals a noise filtration is performed to increase the signal to noise ratio (SNR). A Fourier Transform frequency analysis with a cutoff frequency of 0.9 Hz was performed to remove the electrical noise as well as the environmental noise. On that filtered results, a Butterworth filter was performed to further cleaning of the data.

The first detection signals may be use for normalizing the second detection signals, as they may provide some reference in known conditions (for example minimum or maximum absorbance). For example—linear transformation or non-linear transformation of any second detection signal may be applied.

Assuming, that the set of frequencies a first reference frequency Fmax of maximal absorbance of water, another first reference frequency Fmin of minimal absorbance of water, and K different second frequencies F(1)-F(K). Index k ranges between 1 and K. K and k are integers, K exceeds two. The detection signals obtains by said frequencies are referred to as DS(Fmin), DS(Fmax), and DS(F(1))-DS(F(K)), the normalizing of DF(F(k)) is applied using DS(Fmin) and DS(Fmax).

For example DF(F(k))=[DF(F(k))-DS(Fmin)]/[DS(Fmax)-DS(Fmin)]. Other linear and non-linear normalization functions may be used.

The normalized samples may be then processed by a computerized system for determining the presence and/or concentration of the molecule of interest (for example protein).

The computerized system unit may apply machine learning process (for example artificial intelligence—AI model) and/or a Beer-Lambert law based process. Such detection unit may be trained in a supervised or unsupervised manner.

The training may include providing any number (preferably a vast number that exceeds thousands and even tens of thousands) of samples that include or do not include the molecules of interest.

The training may include obtaining samples from different people of different gender and/or different color and/or of different age, at different times, at different salinity and/or different acidity, and/under different medicinal conditions, and may applied without prior reference urine samples from these people.

The computerized system may include one or more computers, may include one or more processors, may be located (at least in part), in a cloud environment, may be a centralized or distributed computerized system.

Figure 16A:
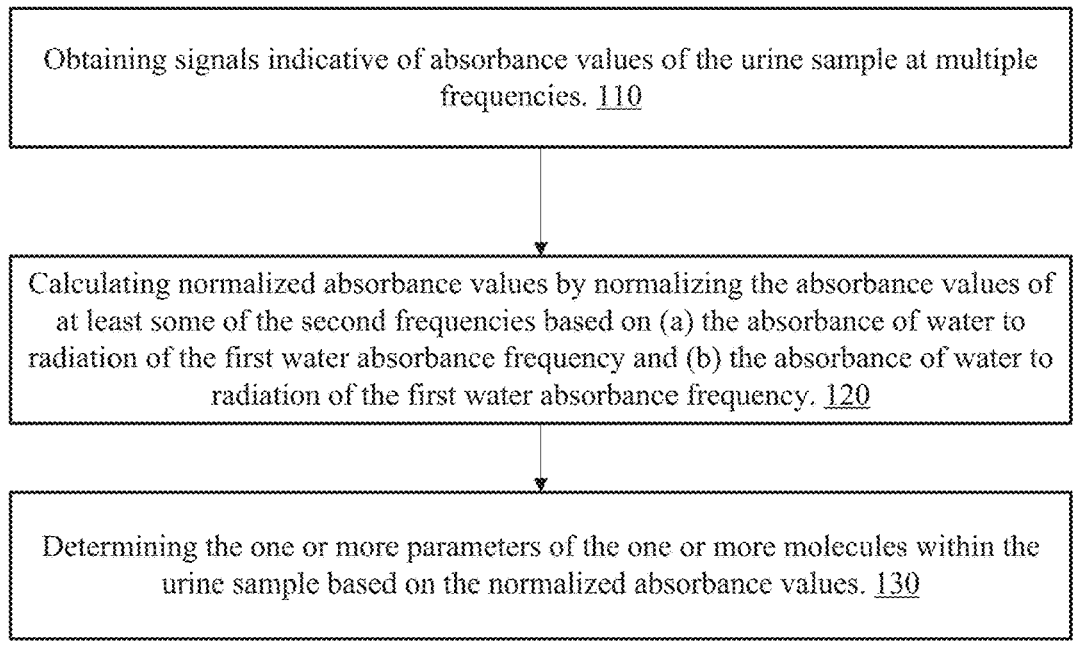
FIG. 16A illustrates an example of a method.

FIG. 16A illustrates method 100 for determining one or more parameters of one or more molecules within a urine sample.

Method 100 may start by step 110 of obtaining signals indicative of absorbance values of the urine sample at multiple frequencies.

The multiple frequencies may include a first water absorbance frequency, second frequencies and a second water absorbance frequency.

The absorbance of water to radiation of the first water absorbance frequency is known.

The absorbance of water to radiation of the first water absorbance frequency is known.

Step 110 may include illuminating a urine sample by radiation of at least the multiple frequencies.

Step 110 may include receiving the signals from another system or process that illuminated the urine sample.

The signals may be represents the intensity of detection signals. The attenuation may be calculated based on the intensity of the transmitted radiation at one or more of the multiple frequencies. The attenuation may be calculated by subtracting (per frequency) the intensity of the detection signal from the intensity of the transmitted signal.

Step 110 may be followed by step 120 of calculating normalized absorbance values by normalizing the absorbance values of at least some of the second frequencies based on (a) the absorbance of water to radiation of the first water absorbance frequency and (b) the absorbance of water to radiation of the first water absorbance frequency.

The normalizing may be applied for each one of absorbance values of the second frequencies.

The one or more parameters may include a presence of the one or more molecules within the urine sample. Additionally or alternatively—the one or more parameters may include a concentration of the of the one or more molecules within the urine sample.

The second frequencies may be located between the first water absorbance frequency and the second water absorbance frequency.

The first water absorbance frequency may be a frequency of minimal absorbance of water.

The second water absorbance frequency may be a frequency of maximal absorbance of water.

The first water absorbance frequency may be a frequency of minimal absorbance of water; and wherein the second water absorbance frequency may be a frequency of maximal absorbance of water.

Step 120 may include one or more out of:

Calculating a reference absorbance difference between (i) an absorbance value of the urine sample at the second water absorbance frequency, and (ii) an absorbance value of the urine sample at the first water absorbance frequency.

Calculating a normalization value of an absorbance value of the urine sample at a second frequency based on (a) a value of an absorbance value of the urine sample at a second frequency, (b) the reference absorbance difference, and at least one of (i) absorbance value of the urine sample at the second water absorbance frequency, and (ii) absorbance value of the urine sample at the first water absorbance frequency.

Calculating a normalization value of an absorbance value of the urine sample at a second frequency by: calculating an absorbance difference between (i) absorbance value of the urine sample at a second frequency, and (ii) the absorbance value of the urine sample at the first water absorbance frequency; and dividing the absorbance difference by the reference absorbance difference.

Calculating a normalization value of an absorbance value of the urine sample at each one of the multiple second frequencies by:

i. Calculating an absorbance difference between (i) absorbance value of the urine sample at a second frequency, and (ii) the absorbance value of the urine sample at the first water absorbance frequency; and ii. dividing the absorbance difference by the reference absorbance difference.

The method may include low pass filtering (applied on absorbance values related to different frequencies), rejection of some high frequency values, and the like.

Step 120 may be followed by step 130 of determining the one or more parameters of the one or more molecules within the urine sample based on the normalized absorbance values.

Step 130 may include at least one out of:

Determining based on normalized absorbance values of test samples of known content. The known content means that a test sample has a predefined concentration of at least one molecule of interest. The test samples may be urine sample in which a certain amount of a certain molecule was added—and at least the increment of the certain molecule is known. The test samples may include a test sample before the controlled increment and after the controlled increment.

Executed by a machine learning process. the machine learning process may be fed with normalized absorbance values of test samples of known content. The known content means that a test sample has a predefined concentration of at least one molecule of interest.

Executed without using a machine learning process.

The multiple frequencies may be spaced apart frequencies.

The multiple frequencies may range between five and twenty spaced apart frequencies.

Figure 16B:
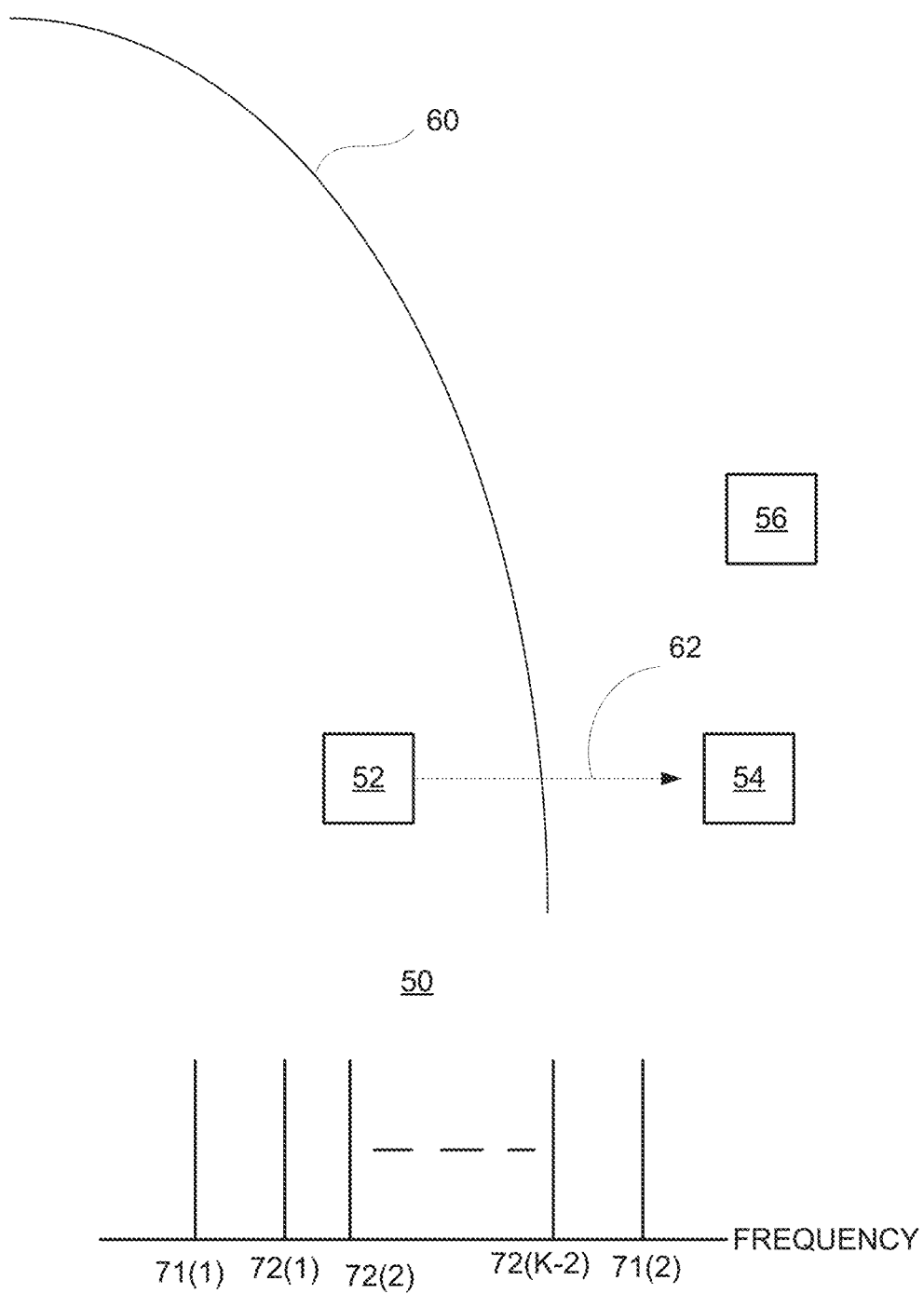
FIG. 16B illustrates an example of a system.

FIG. 16B illustrates a transmitter 52 that transmits radiation that passes through urine sample 60 and a receiver 54 for receiving the attenuated (by urine) radiation—to generate detection signals. A controller and/or processor 56 may determine the attenuation value based on the intensity of the transmitted radiation and the detection signals. The radiation include the multiple frequencies.

The controller and/or generator may apply a machine learning process. Alternatively—the system 50 may send the attenuation values and/or the detection signals or any information regarding the illumination and/or reception processes to a remote computerized system that may perform machine learning processing and the like.

FIG. 16B also illustrates a spectrum that includes first water absorbance frequency 71(1), second frequencies 72(1)-72(K−2), a second water absorbance frequency 71(2)—total of K frequencies.

FIGS. 16C-16F include different sets of points obtained when measuring urine samples of different composition (each set may represent one or multiple—for example 50, 100, 200, 250 samples) of urine samples with known additions (known amount) of one or more molecules. For example—measurements of a first set are represented by rectangles, measurements of a second set are represented by circles, measurements of a third set are represented by empty triangles and measurements of a fourth set are represented by black triangles.

For the testing/learning—any number of sets can be provided. Any manner of knowing at least one concentration of one molecule may be provided.

Each graph includes attenuation values (y-axis) at different frequencies (x-axis)—for one or more test samples of known content (the concentration of a certain molecule is known) at multiple frequencies.

Each set of values may be calculated by averaging multiple measurements of the same test samples.

A set of samples (in multiple frequencies) may be regarded as a signature of a the test sample—for a certain component.

Figure 16C:
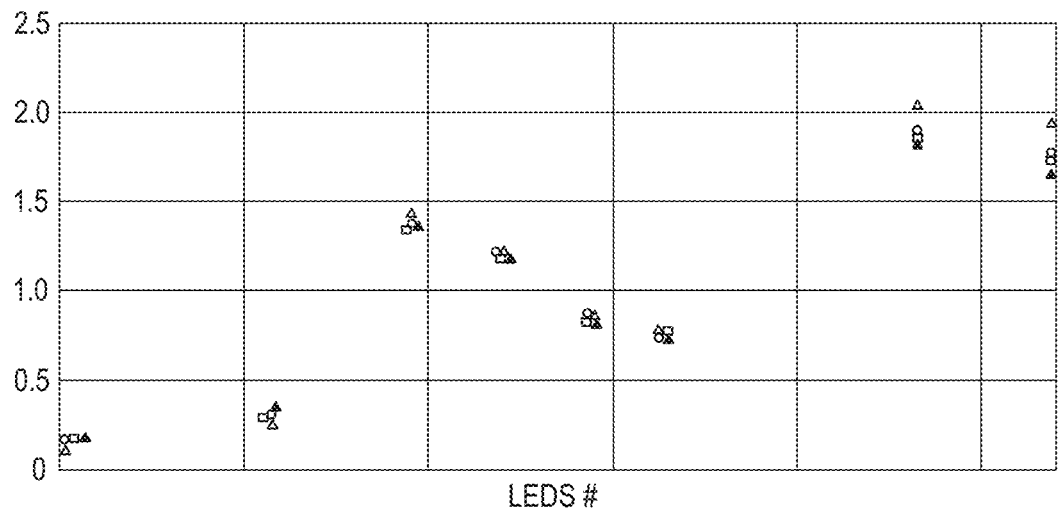
FIGS. 16C-16F illustrate examples of detection signals
Figure 16D:
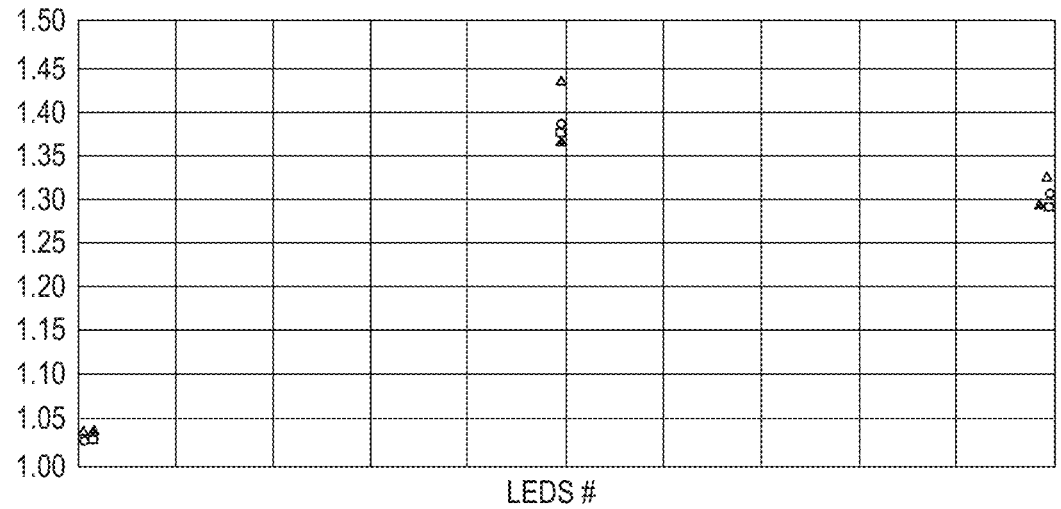
Figure 16E:
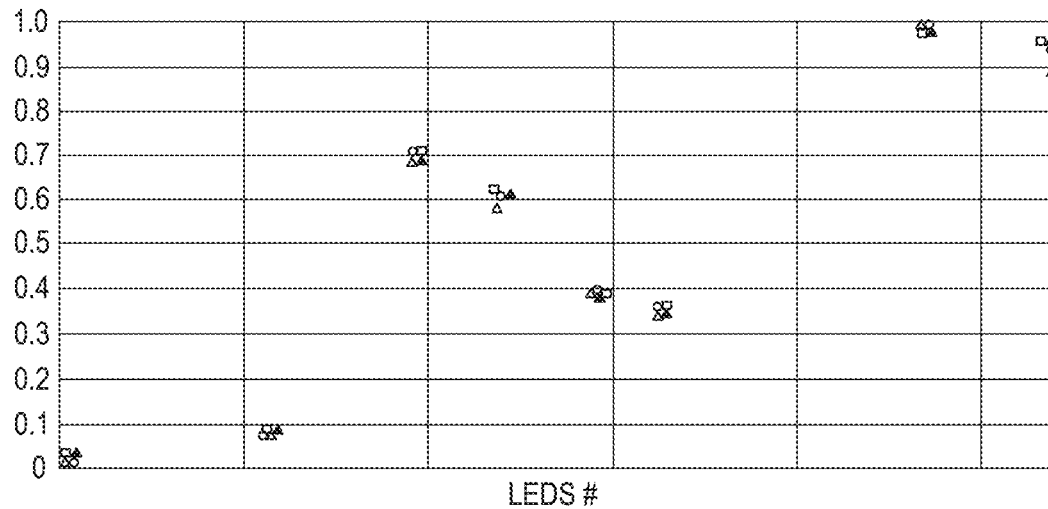
Figure 16F:
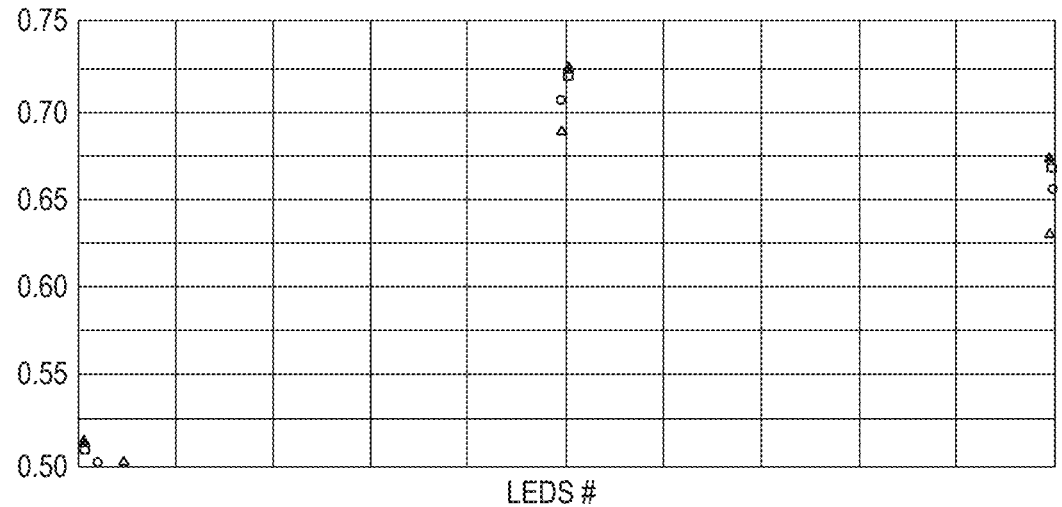

FIGS. 16C and 16D represent attenuation values without normalization and FIGS. 16E and 16F illustrates normalized attenuation values.

In FIGS. 16C and 16D there is no concentration behavior, namely the absorbance is not correlated with concentration changes. In FIGS. 16E and 16F there is a concentration behavior, namely, the absorbance and concentration changes are correlated.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed.

In the foregoing specification, the invention has been described with reference to specific examples of embodiments of the invention. It will, however, be evident that various modifications and changes may be made therein without departing from the broader spirit and scope of the invention as set forth in the appended claims.

Moreover, the terms "front," "back," "top," "bottom," "over," "under" and the like in the description and in the claims, if any, are used for descriptive purposes and not necessarily for describing permanent relative positions. It is understood that the terms so used are interchangeable under appropriate circumstances such that the embodiments of the invention described herein are, for example, capable of operation in other orientations than those illustrated or otherwise described herein.

Furthermore, the terms "assert" or "set" and "negate" (or "deassert" or "clear") are used herein when referring to the rendering of a signal, status bit, or similar apparatus into its logically true or logically false state, respectively. If the logically true state is a logic level one, the logically false state is a logic level zero. And if the logically true state is a logic level zero, the logically false state is a logic level one.

Those skilled in the art will recognize that the boundaries between logic blocks are merely illustrative and that alternative embodiments may merge logic blocks or circuit elements or impose an alternate decomposition of functionality upon various logic blocks or circuit elements. Thus, it is to be understood that the architectures depicted herein are merely exemplary, and that in fact many other architectures may be implemented which achieve the same functionality.

Any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated can also be viewed as being "operably connected," or "operably coupled," to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

Also for example, in one embodiment, the illustrated examples may be implemented as circuitry located on a single integrated circuit or within the same device. Alternatively, the examples may be implemented as any number of separate integrated circuits or separate devices interconnected with each other in a suitable manner.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

It is appreciated that various features of the embodiments of the disclosure which are, for clarity, described in the contexts of separate embodiments may also be provided in combination in a single embodiment. Conversely, various features of the embodiments of the disclosure which are, for brevity, described in the context of a single embodiment may also be provided separately or in any suitable sub-combination.

It will be appreciated by persons skilled in the art that the embodiments of the disclosure are not limited by what has been particularly shown and described hereinabove. Rather the scope of the embodiments of the disclosure is defined by the appended claims and equivalents thereof.

What is claimed is:

1. A system for urine sample analysis, the system comprises:
one or more transmitters for transmitting radiation;
one or more sensors that are configured to receive radiation that passed through the urine sample and to generate detection signals indicative of an intensity of the received radiation at multiple frequencies;
detaching elements that are configured to detach the one or more transmitters and the one or more sensors to a toilet bowl;
a triggering sensor that is configured to sense a condition for triggering an activation of the one or more transmitters and the one or more sensors;
wherein the triggering sensor is a toilet cover motion sensor or a proximity sensor that is configured to sense a presence of a person within a proximity of the toilet bowl and generate a proximity alert; and
a processor that is configured to participate in the urine sample analysis for determining a content of the urine sample based on the detection signals.

2. The system according to claim 1, wherein the triggering sensor is a proximity sensor that is configured to sense a presence of a person within a proximity of the toilet bowl and generate a proximity alert.

3. The system according to claim 1, wherein the triggering sensor is an acoustic sensor.

4. The system according to claim 1, wherein the triggering sensor is a toilet cover motion sensor.

5. The system according to claim 1, wherein the triggering sensor is configured to detect a start of a urination.

6. The system according to claim 1, comprising one or more additional triggering sensors to provide multiple triggering sensors for sense a condition for triggering an activation of the one or more transmitters and the one or more sensors.

7. The system according to claim 1, wherein the detaching element is configured to position the triggering sensor outside the toilet bowl.

8. The system according to claim 1, wherein the detaching element is configured to position the triggering sensor inside the toilet bowl.

9. The system according to claim 1, wherein the one or more sensors are multiple sensors.

10. The system according to claim 9, wherein at least two of the sensors have different fields of view.

11. The system according to claim 9 wherein fields of view of the multiple sensors cover a majority of a virtual horizontal plane of an inner space defined by the toilet bowl.

12. The system according to claim 9, wherein the multiple sensors form a curved one-dimensional array of sensors.

13. The system according to claim 9, wherein the multiple sensors are spaced apart from each other.

14. The system according to claim 9, wherein at least two of the sensors have different spectral responses.

15. The system according to claim 9, wherein at least one sensor is preceded by a spectral filter.

16. The system according to claim 9, wherein at least one sensor is preceded by a tunable spectral filter.

17. The system according to claim 9, wherein at least some of the multiple sensors are at least partially shielded by a rim of the toilet bowl.

18. The system according to claim 9, wherein at least some of the multiple sensors extend outside a rim of the toilet bowl.

19. The system according to claim 1, wherein the processor is configured to control an operation of at least some of the one or more transmitters and the one or more sensors.

20. The system according to claim 1, wherein the one or more transmitters are multiple transmitters and wherein at least some of the multiple transmitters are configured to transmit in a sequential manner.

21. The system according to claim 1, wherein the one or more transmitters are multiple transmitters and wherein at least some of the multiple transmitters are configured to transmit radiation of different frequencies at different points of time.

22. A system for urine sample analysis, the system comprises:
   one or more transmitters for transmitting radiation;
   one or more sensors that are configured to receive radiation that passed through the urine sample and to generate detection signals indicative of an intensity of the received radiation at multiple frequencies;
   detaching elements that are configured to detach the one or more transmitters and the one or more sensors to a toilet bowl;
   triggering sensors to that are configured to sense conditions for triggering an activation of the one or more transmitters and the one or more sensors; and
   a processor that is configured to participate in the urine sample analysis for determining a content of the urine sample based on the detection signals;
   wherein at least two triggering sensors of the triggering sensors differ from each other by a type of sensed event.

23. A system for urine sample analysis, the system comprises:
   one or more transmitters for transmitting radiation;
   multiple sensors that are configured to receive radiation that passed through the urine sample and to generate detection signals indicative of an intensity of the received radiation at multiple frequencies;
   detaching elements that are configured to detach the one or more transmitters and the multiple sensors to a toilet bowl; and
   a processor that is configured to participate in the urine sample analysis for determining a content of the urine sample based on the detection signals;
   wherein at least two sensors of the multiple sensors have partially overlapping fields of view.

* * * * *